(12) United States Patent
Sutton et al.

(10) Patent No.: US 11,028,103 B2
(45) Date of Patent: *Jun. 8, 2021

(54) DERIVATIZED 3-STYRYL-CEPHALOSPORINS

(71) Applicant: Gladius Pharmaceuticals Corporation, Montreal (CA)

(72) Inventors: Larry D. Sutton, Atchison, KS (US); Sophia Yu, Atchison, KS (US)

(73) Assignee: GLADIUS PHARMACEUTICALS CORPORATION, Montreal (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/984,645

(22) Filed: May 21, 2018

(65) Prior Publication Data

US 2018/0319817 A1    Nov. 8, 2018

Related U.S. Application Data

(63) Continuation of application No. 14/775,528, filed as application No. PCT/US2014/024503 on Mar. 12, 2014, now Pat. No. 9,975,905.

(60) Provisional application No. 61/778,378, filed on Mar. 12, 2013.

(51) Int. Cl.
    *C07D 501/60* (2006.01)
    *C07D 501/24* (2006.01)
    *A01N 43/90* (2006.01)
    *C12N 9/99* (2006.01)

(52) U.S. Cl.
    CPC .......... *C07D 501/60* (2013.01); *A01N 43/90* (2013.01); *C07D 501/24* (2013.01); *C12N 9/99* (2013.01)

(58) Field of Classification Search
    USPC ...................................................... 546/112
    See application file for complete search history.

(56) References Cited

U.S. PATENT DOCUMENTS

| | | |
|---|---|---|
| 3,830,700 A | 8/1974 | O'Callaghan et al. |
| 3,971,778 A | 7/1976 | Cook et al. |
| 3,983,113 A | 9/1976 | Beeby |
| 4,065,620 A | 12/1977 | Webber |
| 4,094,978 A | 6/1978 | Beeby |
| 4,103,084 A | 7/1978 | Bradshaw et al. |
| 4,152,432 A | 5/1979 | Heymes et al. |
| 4,255,423 A | 3/1981 | Beattie et al. |
| 4,258,040 A | 3/1981 | Christensen et al. |
| 4,264,595 A | 4/1981 | Numata et al. |
| 4,307,116 A | 12/1981 | Farge et al. |
| 4,307,233 A | 12/1981 | Farge et al. |
| 4,342,758 A | 8/1982 | Firestone |
| 4,346,218 A | 8/1982 | Tsuji et al. |
| 4,365,062 A | 12/1982 | Farge et al. |
| 4,380,512 A | 4/1983 | Gottstein |
| 4,385,181 A | 5/1983 | Farge et al. |
| 4,388,326 A | 6/1983 | Firestone |
| 4,500,457 A | 2/1985 | Gosteli et al. |
| 4,520,022 A | 5/1985 | Hoshi et al. |
| 4,520,193 A | 5/1985 | Berger et al. |
| 4,558,071 A | 12/1985 | Firestone |
| 4,616,084 A | 10/1986 | Habich et al. |
| 4,639,448 A | 1/1987 | Takaya et al. |
| 4,654,359 A | 3/1987 | Firestone |
| 4,692,517 A | 9/1987 | Skotnicki et al. |
| 4,760,067 A | 7/1988 | Firestone |
| 4,839,350 A | 6/1989 | Atsumi et al. |
| 4,855,420 A | 8/1989 | Jung |
| 4,870,168 A | 9/1989 | Baker et al. |
| 4,874,856 A | 10/1989 | Iimura et al. |
| 4,952,690 A | 8/1990 | Gosteli et al. |
| 4,988,686 A | 1/1991 | Atsumi et al. |
| 5,061,702 A | 10/1991 | Atsumi et al. |
| 5,073,551 A | 12/1991 | Kobori et al. |
| 5,151,417 A | 9/1992 | Sasho et al. |
| 5,171,854 A | 12/1992 | Schmidt et al. |
| 5,324,721 A | 6/1994 | Schneider et al. |
| 5,336,768 A | 8/1994 | Albrecht et al. |
| 5,373,001 A | 12/1994 | Aszodi et al. |
| 5,401,841 A | 3/1995 | Gerd et al. |
| 5,438,052 A | 8/1995 | Angehrn et al. |
| 5,470,972 A | 11/1995 | Torii et al. |

(Continued)

FOREIGN PATENT DOCUMENTS

| | | |
|---|---|---|
| CA | 1340154 C | 12/1998 |
| CA | 1340424 C | 3/1999 |

(Continued)

OTHER PUBLICATIONS

Albrecht et al. (1991) "Dual-Action cephalosporins: Cephalosporin 3'-Quinolone Carbamates," J. Med. Chem. 34:2857-2864.
Ambler (1980) "The Structures of R-Lactamases," Philos. Trans. R. Sci. Lond. B. Biol. Sci. 289:321-323.
Aszodi et al. (1993) "Vinylogous vs. Arylogous Isocephems" Bioorganic Med. Chem. Letts 3(11):2231-2236 (Pergamon Press).
Bird et al. (1992) "Pharmacokinetics of catechol cephalosporins. The effect of incorporating substituents into the catechol moiety on pharmacokinetics in a marmoset model," Journal of Medicinal Chemistry. 35:2643-2651.

(Continued)

*Primary Examiner* — Nizal S Chandrakumar
(74) *Attorney, Agent, or Firm* — Perkins Coie LLP

(57) ABSTRACT

Broad spectrum beta-lactamase inhibitors. Certain inhibitors also exhibit potent antibiotic activity in addition to beta-lactamase inhibition. Compounds of the invention are designed such that on cleavage of the beta-lactam ring reactive moieties are generated which can inactivate beta-lactamase. Also provided are methods of making beta-lactamase inhibitors and beta-lactam antibiotics exhibiting such inhibition. Additionally provided are pharmaceutical compositions for treatment or prevention of bacterial infections and methods of treatment of such infections.

11 Claims, 6 Drawing Sheets

(56) References Cited

U.S. PATENT DOCUMENTS

| | | | |
|---|---|---|---|
| 5,541,175 A | 7/1996 | Yeo et al. | |
| 5,656,754 A | 8/1997 | Torii et al. | |
| 5,854,227 A | 12/1998 | Hartmann et al. | |
| 5,936,083 A | 8/1999 | Aszodi et al. | |
| 6,133,441 A | 10/2000 | Wagner | |
| 6,248,881 B1 | 6/2001 | Wieser et al. | |
| 6,417,351 B1 | 7/2002 | Kameyama | |
| 6,576,761 B1 | 6/2003 | Tanaka et al. | |
| 6,897,304 B2 | 5/2005 | Kawashima et al. | |
| 8,883,772 B2* | 11/2014 | Sutton | A01N 43/90 514/200 |
| 9,453,032 B2 | 9/2016 | Sutton et al. | |
| 9,809,605 B1 | 11/2017 | Sutton et al. | |
| 9,862,729 B2* | 1/2018 | Sutton | C07D 501/24 |
| 9,975,905 B2* | 5/2018 | Sutton | A61P 31/00 |
| 10,000,509 B2 | 6/2018 | Sutton et al. | |
| 10,239,890 B2* | 3/2019 | Sutton | A01N 43/90 |
| 2005/0124580 A1 | 6/2005 | Freire et al. | |
| 2008/0200447 A1 | 8/2008 | Koppel | |
| 2009/0131394 A1 | 5/2009 | Sutton et al. | |
| 2010/0231700 A1 | 9/2010 | Jalbout et al. | |
| 2010/0261700 A1 | 10/2010 | Sutton et al. | |
| 2015/0011524 A1 | 1/2015 | Sutton et al. | |

FOREIGN PATENT DOCUMENTS

| | | |
|---|---|---|
| DE | 2727753 A1 | 3/1978 |
| EP | 25857 A1 | 4/1981 |
| EP | 292808 A2 | 11/1988 |
| EP | 408034 A1 | 1/1991 |
| EP | 477717 A2 | 4/1992 |
| EP | 623622 A1 | 11/1994 |
| EP | 691343 A1 | 1/1996 |
| EP | 357089 B1 | 3/1996 |
| EP | 1325923 A1 | 7/2003 |
| GB | 1488679 A | 10/1977 |
| JP | S55-154980 A | 12/1980 |
| JP | S61-178991 A | 8/1986 |
| JP | S63-211286 A | 9/1988 |
| JP | S63-307885 A | 12/1988 |
| JP | H02-69484 A | 3/1990 |
| JP | H03-5486 A | 1/1991 |
| JP | H04-273882 A | 9/1992 |
| JP | H06-145176 A | 5/1994 |
| JP | H08-283273 A2 | 10/1996 |
| JP | H09-003074 A | 1/1997 |
| JP | 2011/500586 A | 1/2011 |
| WO | 8402911 A1 | 8/1984 |
| WO | 9316043 A1 | 8/1993 |
| WO | 9429320 A1 | 12/1994 |
| WO | 2009049086 A1 | 4/2009 |
| WO | 2010118361 A1 | 10/2010 |

OTHER PUBLICATIONS

Bodor (1985) "Targeting of drugs to the brain," Methods in Enzymology. 112:381-396.

Boucher et al. (Apr. 17, 2013) "10 x '20 Progress-Development of New Drugs Active Against Gram-Negative Bacilli: An Update From the Infectious Diseases Society of America," Clin. Infect. Dis. pp. 1-10.

Boyd et al. (1979) "Electronic Structures of Cephalosporins and Penicillins. 9. Departure of a Leaving Group in Cephalosporins," J. Med. Chem. 22(7):778-784.

Bundgaard (1985) "Formation of prodrugs of amines, amides, ureides, and imides," Methods in Enzymology. 112:347-359.

Bundgaard (1991) "Design and Application of Prodrugs," Ch. 5 In; A Textbook of Drug Design and Development. Ed.: Krosgaard-Larsen et al. pp. 113-191.

Bundgaard (1992) "Means to enhance penetration: (1) Prodrugs as a means to improve the delivery of peptide drugs" Advanced Drug Delivery Review. 8:1-38.

Bush et al. (2010) "Updated Functional Classification of 13-Lactamases," Antimicrob. Agents Chemother. 54:969-976.

Buynak (2006) "Understanding the Longevity of the 13-Lactam Antibiotics and of Antibiotic/β-Lactamase Inhibitor Combinations," Biochem. Pharmacol. 71 :930-940.

Buynak (2013) "β-Lactamase inhibitors: a review of the patent literature 2010 -2013," Expert Opin. Ther. Pat. 23(11):1469-1481.

Buynak et al. (2004) "The Discovery and Development of Modified Penicillin- and Cephalosporin-Derived β-Lactamase Inhibitors," Current Medicinal Chemistry. 11 :1951-1964.

Charton (1985) "Prodrug lability prediction through the use of substituent effects," Methods in Enzymology. 112:323-340.

Cornaglia et al. (2011) "Metallo-β-lactamases: a last frontier for β-lactams?" Lancet Infect. Dis.11(5):381-393.

Danishuddin et al. (Aug. 2013) "Blad: A comprehensive database of widely circulated Beta-lactamases," Bioinformatics, 29(19):2515-2516.

Dorwald F.A. Side Reactions in Organic Synthesis, 2005, Wiley: VCH, Weinheimpg. IX of Preface p. 1-15.

Drawz et al. (Jan. 2010) Three Decades of β-Lactamase Inhibitors, Clin. Microbial. Rev. 23(1):160-201.

Fina et al. (Jan. 26, 1973) "The Alpha Effect. A Review," Int. J. Chem. Kinetics 5(1 ):1-26.

Fisher et al. (Web Release Feb. 9, 2005) "Bacterial Resistance to β-Lactam Antibiotics: Compelling Opportunism, Compelling Opportunity," Chem. Rev. 105:395-424.

Fleisher et al. (1985) "Design of prodrugs for improved gastrointestinal absorption by intestinal enzyme targeting," Methods in Enzymology. 112:360-381.

Goossens et al. (Sep. 5, 1998) "Community Acquired Infections and Bacterial Resistance," British Med. J. 317:654-657.

Grekov et al. (1978) The Alpha-Effect in the Chemistry of Organic Compounds, Russian Chem. Rev. 47(7):631-648.

Harmoinen et al. (2003) "Enzymic degradation of a β-lactam antibiotic, ampicillin, in the gut: a novel treatment modality," J. Antimicrob. Chemother. 51 :361-365.

Hickey et al. (May 2007) "Hydrates and Solid-State Reactivity: A Survey of β-Lactam Antibodies," J. Pharmaceutical Sci. 96(5):1090-1099.

Hooton et al. (Mar. 2001) "Antimicrobial Resistance: A Plan of Action for Community Practice," Am. Fam. Physician 63(6):1087-1096; American Academy of Family Physicians.

Jamieson et al. (Aug. 2003) "In Vitro Activities of Novel Oxapenems, Alone and in Combination with Ceftazidime, Against Gram-Positive and Gram-Negative Organisms," Antimicrob. Agents Chemother. 47(8):2615-2618.

Jones (Feb. 2001) "Resistance Patterns Among Nosocomial Pathogens—Trends Over the Past Few Years," Chest 119(2):397S-404S (supp).

Jones et al. (1999) "Epidemiologic Trends in Nosocomial and Community-Acquired Infections Due to Antibiotic-Resistant Gram-Positive Bacteria: The Role of Streptogramins and Other Newer Compounds," Diagn. Microbial. Infect. Dis. 33:101-112.

Jung et al. (1998) "Synthesis and Antibacterial Activity of C3-(Substituted )vinyl Cephalosporins," Korean Journal of Medicinal Chemistry. 8(2):92-95.

Koh et al. (1996) "Synthesis and Structure-Activity Relationship of Cephalosporins having a Cetechol Moeity," Korean Journal of Medicinal Chemistry. 6:333-338.

Lahey Clinic (Oct. 22, 2015) "β-Lactamase Classification and Amino Acid Sequences for TEM, SHV and OXA Extended-Spectrum and Inhibitor Resistant Enzymes," Lahey Clinic Foundation, Inc. http://www.lahey.org/Studies. [Last Accessed Sep. 22, 2016].

Lee et al. (Web Release Dec. 2, 2004) "A Practical Synthesis of Nitrocefin," J. Org. Chem. 70(1) :367-369.

McArthur et al. (Jul. 2013) "The Comprehensive Antibiotic Resistance Database," Antimicrobial Agents & Chemotherapy, 57(7):3348-3357.

McDonald et al. (Jun. 15, 2012) "Enzymes: Irreversible Inhibition," eLS. John Wiley & Sons. pp. 1-17.

Naito et al. (1987) "Synthesis and Structure-Activity Relationship of a New Oral Cephalosporin, BMY-28100 and Related Compounds" Journal Antibiotics (Tokoyo) XL(7) :991-1005.

(56) References Cited

OTHER PUBLICATIONS

Nelson (1985) "Alteration of drug metabolism by the use of prodrugs," Methods in Enzymology. 112:340-347.
Nielsen et al. (1988) "Glycolamide Esters as Biolabile Prodrugs of Carboxylic Acid Agents: Synthesis, Stability, Bioconversion, and Physicochemical Properties," Journal of Pharmaceutical Sciences. 77:285-298.
Nogrady (1985) "Pro-Drugs and Soft Drugs," Ch. 4, In; Medicinal Chemistry a Biochemical Approach. Oxford University Press. New York, New York. pp. 388-392.
Notari (1985) "Theory and practice of prodrug kinetics," Methods in Enzymology. 112:309-332.
Peleg et al. (2010) "Hospital-Acquired Infections Due to Gram-Negative Bacteria," New England Journal of Medicine. 362(19):1804-1813.
PubChem Compound. CID No. 21772243. Accessible on the Internet at URL: https://pubchem.ncbi.nlm.nih.gov/compound/21772243. [Last Accessed Jun. 12, 2014].
PubChem Compound. CID No. 22817635. Accessible on the Internet at URL: https://pubchem.ncbi.nlm.nih.gov/compound/22817635. [Last Accessed Jun. 12, 2014].
PubChem Compound. CID No. 54191938. Accessible on the Internet at URL: https://pubchem.ncbi.nlm.nih.gov/compound/54191938. [Last Accessed Jun. 11, 2014].
PubChem Compound. CID No. 58844721. Accessible on the Internet at URL: https://pubchem.ncbi.nlm.nih.gov/compound/58844721. [Last Accessed Jun. 12, 2014].
PubChem Compound. CID No. 60173106. Accessible on the Internet at URL: https://pubchem.ncbi.nlm.nih.gov/compound/60173106. [Last Accessed Jul. 22, 2016].
PubChem Compound. CID No. 71714552. Accessible on the Internet at URL: https://pubchem.ncbi.nlm.nih.gov/compound/71714552. [Last Accessed Jul. 22, 2016].
PubChem Compound. CID No. 9957982. Accessible on the Internet at URL: https://pubchem.ncbi.nlm.nih.gov/compound/9957982. [Last Accessed Jun. 11, 2014].
Queijo (1955) "From Ancient Molds to Modern Miracles: The Discovery of Antibiotics," Ch. 7 In; Breakthrough! How the 10 Greatest Discoveries in Medicine Saved Millions, From Ancient Molds to Modern Miracles: The Discovery of Antibiotics. FT Press Science. Pearson Education, Inc. New Jersey. pp. 138-160.
Sandanayaka et al. (2002) "Resistance to 13-Lactam Antibiotics: Structure and Mechanism Based Design of 13-Lactamase Inhibitors," Curr. Med. Chem. 9:1145-1165.
Shlaes (Jan. 24, 2013) "New β-lactam-β-lactamase inhibitor combinations in clinical development," Ann. N. Y. Acad. Sci. 1277:105-114.
Sutton et al. (1995) "Development, Characterization, and Initial Evaluations of S1—A New Chromogenic Cephalosporin for β-Lactamase Detection," Diag. Microbial. Infect. Dis. 21 :1-8.
Sutton L.D. et al. (Sep. 2013) "Inhibitor-Stabilization of NDM-1 Azanide Intermediate Increases Residence Time and Inhibition Potency," Poster F-1205 53rd Interscience Conference on Antimicrobial Agents and Chemotherapy, Denver CO sponsored by the American Society for Microbiology.
Sutton, L.D. et al. (Sep. 2013) "Mechanism-Based Cephalosporin Inhibitors of Metallo- and Serine-Carbapenemases," Poster 1204 53rd Interscience Conference on Antimicrobial Agents and Chemotherapy, Denver Co sponsored by the American Society for MicrobioloQy.
Sutton, L.D. et al. (Sep. 2013) "Rationally Designed Suicide Inhibitor of NDM-1 with Anti-Bacterial Activity," Poster F-1205a 53rd Interscience Conference on Antimicrobial Agents and Chemotherapy, Denver CO sponsored by the American Society for Microbiology.
Sutton, L.D. et al. (Sep. 2013) "Suicide Inhibition of NDM-1 by the Cephalosporin 5200 is Mapped Using Cys208 and Lys211 Variants," Poster 1205b 53rd Interscience Conference on Antimicrobial Agents and Chemotherapy, Denver CO sponsored by the American Society for Microbiology.

Tanaka et al. (2001) "Reductive Cross-Coupling of 3-Substituted Delta3-Cephems with Alkenyl Halides in an Al/PbBr2/NiBr2(bpy) Triplemetal Redox System. Synthesis of 3-Alkenyl-Delta3-cephems," Journal of Organic Chemistry. 66:570-577.
Toney et al. (2001) "Succinic Acids as Potent Inhibitors of Plasmid-borne IMP-1 Metallo-β-lactamase" J. Biol. Chem. 24:31913-31918.
Venkatesh et al. (Feb. 2000) "Role of the development scientist in compound lead selection and optimization" J. Pharm. Sci., 89, pp. 145-154.
Wagner et al. (2009) "Modeling, Synthesis and Biological Evaluation of Potential Retinoid X Receptor (RXR) Selective Agonists: Novel Analogues of 4-[1-(3,5,5,8,8-Pentamethyl-5,6, 7,8-tetrahydro-2-naphthypethynyl]benzoic Acid (Bexarotene)," J. Med. Chem. 52(19) :5950-5966.
Wilke et al. (2005) "β-Lactam Antibiotic Resistance: A Current Structural Perspective," Curr. Opni. Microbial. 8:525-533.
Wright (2011) "Molecular mechanisms of antibiotic resistance," Chem Commun 47:4055-4061.
Yamazaki et al. (2000) "Novel Cephalosporins 2. Synthesis of 3-Heterocyclic-fused Thiopyranylthiovinyl Cephalosporins and Antibacterial Activity against Methicillinresistant *Staphylococcus aureus* and Vancomycin-resistant Enterococcus faecalis," Journal of Antibiotics. 53:546-550.
Yu et al. (Jun. 16, 2012) "A chromogenic cephalosporin for β-lactamase inhibitor screening assays," Analytical Biochemistry. 438:96-98.
Zhanel et al. (Feb. 2013) "Ceftazidime-Avibactam: a Novel Cephalosporin/β-lactamase Inhibitor Combination," Drugs 73(2):159-177.
EPO, Examination Report corresponding to European Patent Application No. 08837969.8, dated Nov. 5, 2014.
EPO, Extended European Search Report corresponding to European Patent Application No. 08837969.8, dated Jun. 25, 2013.
EPO, Extended European Search Report corresponding to European Patent Application No. 14778768.3, dated Aug. 5, 2016.
EPO, Extended European Search Report corresponding to European Patent Application No. 18196405.7, dated Oct. 30, 2018. 8 pages.
JPO, Notice of Reasons for Rejection corresponding to Japanese Patent Application No. P2010-529054, dated Aug. 19, 2014—with English translation.
JPO, Notice of Reasons for Rejection corresponding to Japanese Patent Application No. P2010-529054, dated Jul. 23, 2013—with English translation.
JPO, Notice of Reasons for Rejection corresponding to Japanese Patent Application No. P2016-501556, dated Jan. 9, 2017—with English translation. 12 pages.
JPO, Notice of Reasons for Rejection corresponding to Japanese Patent Application No. P2018-130159, dated May 7, 2019—with English translation. 7 pages.
USPTO, Final Office Action corresponding to U.S. Appl. No. 14/775,528, dated Jun. 7, 2017. 9 pages.
USPTO, Non-Final Office Action corresponding to U.S. Appl. No. 14/775,528, dated Oct. 25, 2016. 15 pages.
USPTO, Notice of Allowance corresponding to U.S. Appl. No. 14/775,528, dated Jan. 19, 2018. 8 pages.
USPTO, Restriction Requirement corresponding to U.S. Appl. No. 14/775,528, dated Jun. 23, 2016. 7 pages.
WIPO, International Preliminary Report on Patentability corresponding to International Patent Application No. PCT/US2014/024503, completed Feb. 21, 2015.
WIPO, International Search Report and Written Opinion, Corresponding to International Application No. PCT/US2008/079410, dated Dec. 12, 2008.
WIPO, International Search Report and Written Opinion, Corresponding to International Application No. PCT/US2010/030590, dated Jun. 28, 2010.
WIPO, International Search Report with Written Opinion corresponding to International Patent Application No. PCT/US2014/024503, dated Jul. 15, 2014.
CIPO, Office Action received for Canadian patent application No. 2,905,240, dated Apr. 27, 2020. 22 pages.
EPO, Office Action received in European patent application No. 18196405.7, dated Dec. 13, 2019. 3 pages.

(56) References Cited

OTHER PUBLICATIONS

JPO, Notice of Reasons for Rejection for Japanese patent application No. P2018-130159, dated Feb. 25, 2020. 6 pages with English translation.

* cited by examiner

Cephalosporin

Cephamycin

Carbacephem

DERIVATIZED 3-STYRYL-CEPHALOSPORINS

CROSS-REFERENCE TO RELATED APPLICATIONS

This application is a continuation of U.S. application Ser. No. 14/775,528, filed Sep. 11, 2015, which is a U.S. National Stage application under 35 U.S.C. 371 of PCT/US2014/024503, filed in English on Mar. 12, 2014, which claims the benefit of U.S. provisional application U.S. 61/778,378, filed on Mar. 12, 2013. Each of these applications is incorporated by reference herein in its entirety.

BACKGROUND

The discovery, development, and use of antibiotics to prevent and cure bacterial infections is one of the great milestones of modern medicine (Queijo, Jon. *Breakthrough!: How the 10 Greatest Discoveries in Medicine Saved Millions*, From Ancient Molds to Modern Miracles: The Discovery of Antibiotics. Chapter 7, FT Press Science (Pearson Education, Inc.), New Jersey, pp. 138-160). The β-lactam class of antibiotics has been one of our safest and most effective antibacterial agents (Hannoinen, J; Vaali, K; Koski, P; Syrjanen, K; Laitinen, O; Lindevall, K; Westermarck, E. (2003) Enzymic degradation of a β-lactam antibiotic, ampicillin, in the gut: a novel treatment modality J Antimicrob Chemother 51, 361-365). Since their introduction, bacteria have developed resistance to these antibiotics (Wright, G O (2011) Molecular mechanisms of antibiotic resistance. *Chem Commun* 47, 4055-4061). Bacterial production of β-lactamases, enzymes that inactivate β-lactam antibiotics through the catalytic hydrolysis of their lactam ring, is the most important and prevalent mechanism of resistance (Fisher. J. F., Meroueh, S O and Mobashery, S (2005) Bacterial resistance to-lactam antibiotics: compelling opportunism, compelling opportunity. *Chem Rev* 105, 395-424). Today there are over 1500 β-lactamases reported β-Lactamase Classification and Amino Acid Sequences for TEM, SHY and OXA Extended-Spectrum and Inhibitor Resistant Enzymes, http://www.lahey.org/Studies/, accessed 10 Mar. 2014 and Site Web Institut Pasteur β-lactamase enzyme variants, http://www.pasteur.fr/ip/easysite/pasteur/en/research/plates-formes-technologiques/pasteur-genopole-ile-de-france/genotyping-of-pathogens-and-public-health-pf8/β-lactamase-enzyme-variants/β-lactamase-enzyme-variants accessed 10 Mar. 2014). There are now enzymes that inactivate every known class of β-lactam antibiotics (Peleg, A Y; Hooper, D C (2010) Hospital-Acquired Infections Due to Gram-Negative Bacteria. *N Engl J Med* 362:19, 1804-1813)

There are two families of β-lactamases, serine and zinc-dependent, that are divided into three functional classes according to Bush and Jacoby (Bush, K; Jacoby, J A, (2010) Updated Functional Classification of -Lactamases. *Antimicrob Agents Chemother* 54, 969-976). Classes 1 and 2 are serine enzymes that catalyze hydrolysis of β-lactam rings via a covalent intermediate known as an acylenzyme and Class 3 enzymes which are $Zn^{2+}$-dependent and catalyze hydrolysis of lactam rings via direct nucleophilic attack of an active site hydroxide anion.

Previous attempts to circumvent β-lactamase-mediated antibiotic resistance can be divided into two strategies. The first, adding bulky functional groups to β-lactam antibiotics to make them poor β-lactamase substrates while maintaining their antibacterial activities has largely been circumvented by bacteria as there are now β-lactamases that inactivate every known clinically-approved β-lactam on the market (Peleg, A Y; Hooper, D C (2010) Hospital-Acquired Infections Due to Gram-Negative Bacteria. N Engl J Med 362:19, 1804-1813).

The second strategy has been the use of β-lactamase inhibitors in combination with β-lactam antibiotics. There are three clinically approved serine-β-lactamase inhibitors that have been used for decades (Drawz, S M; Bonomo, R A, (2010) Three Decades of β-Lactamase Inhibitors. Clin Microbial Rev 23, 160-201). Today these compounds are increasingly ineffective at protecting antibiotics from degradation by β-lactamase catalysis as selective pressure has led to the evolution of several inhibitor-resistant β-lactamases including groups 1, 1e, 2br, and 2ber as well as some group 2d, 2de, 2df and 2f enzymes. There are two serine-β-lactamase inhibitors in later stages of clinical development, Avibactam and MK-7655 (Boucher, H. W.; Talbot, G. H.; Benjamin, D. K.; Bradley, J.; Guidos, R. J.; Jones, R. N.; Murray, B. E.; Bonomo, R. a; Gilbert, D. (2013) 10×'20 Progress—Development of New Drugs Active Against Gram-Negative Bacilli: An Update From the Infectious Diseases Society of America. Clin. Infect. Dis. 1-10; Shlaes, D. M. (2013) New β-lactam-β-lactamase inhibitor combinations in clinical development. Ann. N. Y. Acad. Sci. 1277, 105-14; Buynak, J. D. (2013) β-Lactamase inhibitors: a review of the patent literature 2010-2013. Expert Opin. Ther. Pat. 1-13; AstraZeneca-Our pipeline, http://www.astrazeneca.com/Research/Our-pipeline-summary, accessed 26 Feb. 2013). However, there remains some question about whether Avibactam is effective in inhibiting group 2d, 2de, and 2df enzymes and data suggest its combination with ceftazidime is ineffective versus Acenitobacter spp and anaerobic organisms (Zhanel, G G; Lawson, C D; Adam, H; Schweizer, F; Zelenitsky, S; Lagace-Wiens, P R; Denisuik, A; Rubinstein, E; Gin, A S; Hoban, O J; Lynch, J P 3rd; Karlowsky, J A (2013) Ceftazidime-Avibactam: a Novel Cephalosporin/β-lactamase Inhibitor Combination. Drugs 73:2, 159-177)

All of the β-lactamase inhibitors, approved and in development, bind at β-lactamase-active sites and require the formation of a covalent intermediate with the enzyme before β-lactamase inactivation can occur. Since none of the group 3 metallo-β-lactamases form a covalent intermediate with their substrates or inhibitors, all of these inhibitors are ineffective against group 3 β-lactamases (Cornaglia, G; GiamarellouH; Rossolini, G M (2011) Metallo-β-lactamases: a last frontier for β-lactams? *Lancet Infect Dis* 11:5, 381-393).

Another drawback of these known β-lactamase inhibitors is that they have no intrinsic, potent antibacterial activities. Thus there is an important need for β-lactam antibiotic compounds that also possess potent and broad spectrum β-lactamase inhibiting properties.

SUMMARY OF THE INVENTION

The invention relates to β-lactam compounds which are β-lactamase inhibitors or inactivators and particularly relates to β-lactam antibiotics that also exhibit inhibition or inactivation of β-lactamases. The invention is further directed to methods of making such compounds and methods of using such compounds for inhibition of microbial growth and treating infectious diseases.

In an embodiment, the invention provides compounds of formula I-V and IA-IIIA:

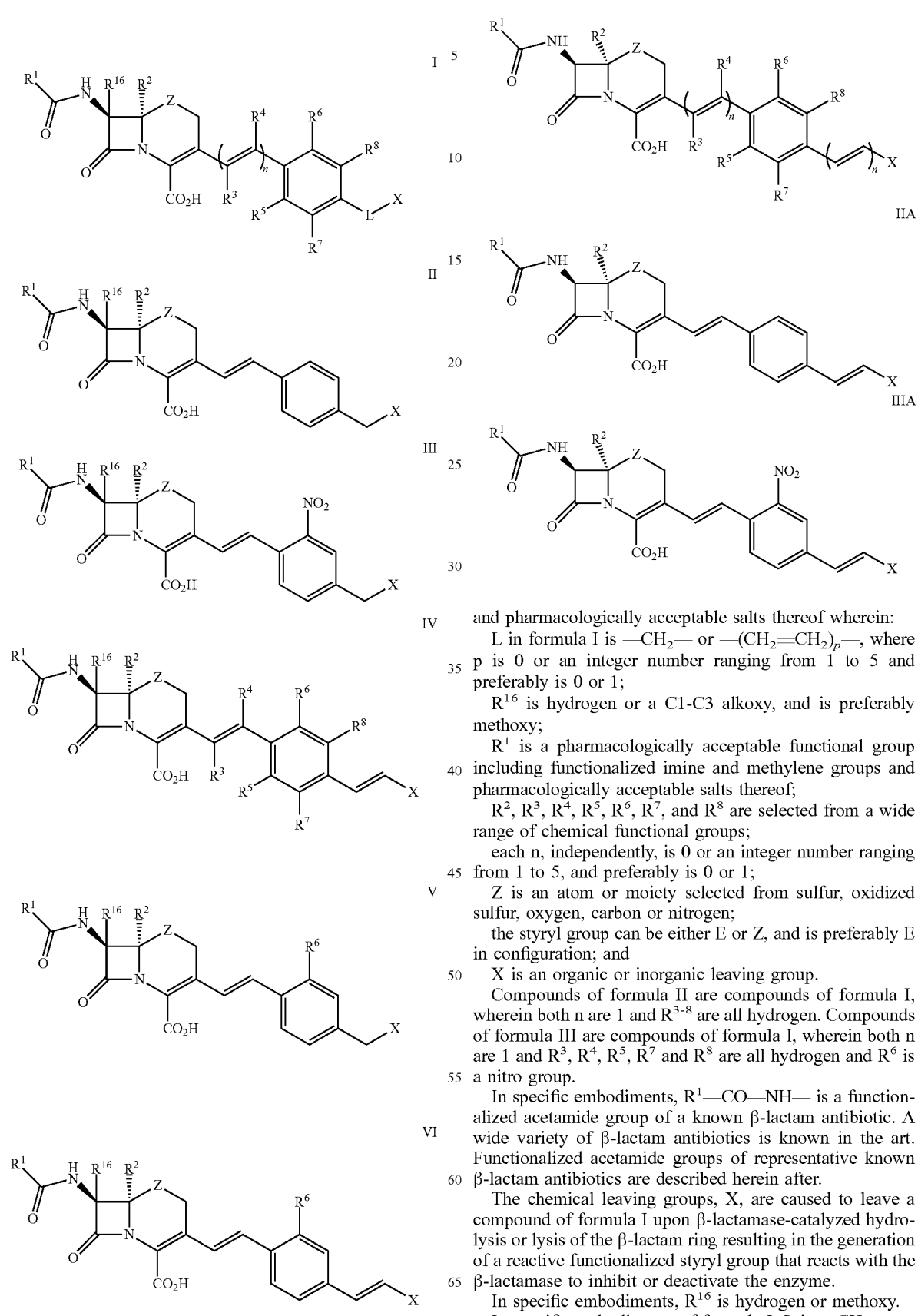

and pharmacologically acceptable salts thereof wherein:

L in formula I is —$CH_2$— or —($CH_2$=$CH_2$)$_p$—, where p is 0 or an integer number ranging from 1 to 5 and preferably is 0 or 1;

$R^{16}$ is hydrogen or a C1-C3 alkoxy, and is preferably methoxy;

$R^1$ is a pharmacologically acceptable functional group including functionalized imine and methylene groups and pharmacologically acceptable salts thereof;

$R^2$, $R^3$, $R^4$, $R^5$, $R^6$, $R^7$, and $R^8$ are selected from a wide range of chemical functional groups;

each n, independently, is 0 or an integer number ranging from 1 to 5, and preferably is 0 or 1;

Z is an atom or moiety selected from sulfur, oxidized sulfur, oxygen, carbon or nitrogen;

the styryl group can be either E or Z, and is preferably E in configuration; and X is an organic or inorganic leaving group.

Compounds of formula II are compounds of formula I, wherein both n are 1 and $R^{3-8}$ are all hydrogen. Compounds of formula III are compounds of formula I, wherein both n are 1 and $R^3$, $R^4$, $R^5$, $R^7$ and $R^8$ are all hydrogen and $R^6$ is a nitro group.

In specific embodiments, $R^1$—CO—NH— is a functionalized acetamide group of a known β-lactam antibiotic. A wide variety of β-lactam antibiotics is known in the art. Functionalized acetamide groups of representative known β-lactam antibiotics are described herein after.

The chemical leaving groups, X, are caused to leave a compound of formula I upon β-lactamase-catalyzed hydrolysis or lysis of the β-lactam ring resulting in the generation of a reactive functionalized styryl group that reacts with the β-lactamase to inhibit or deactivate the enzyme.

In specific embodiments, $R^{16}$ is hydrogen or methoxy.

In specific embodiments of formula I, L is —$CH_2$—.

In specific embodiments of formula I, n is an integer from 1-5 and L is —(CH=CH)$_p$—.

In specific embodiments of formula II, when $R^{16}$ is hydrogen, Z is an atom or moiety other than —S—.

In specific embodiments of formula II, when $R^{16}$ is hydrogen and Z is —S—, X is other than a halogen or group 4 of FIG. 5.

In specific embodiment of any of the above formulas, $R^2$ is hydrogen.

In specific embodiments of formulas IV and IA, both n are 1.

In specific embodiments, Z is —S— and $R^{16}$ is methoxy; Z is —CH$_2$—

In specific embodiments, one or more of $R^5$-$R^8$ are —NO$_2$ groups. In specific embodiments, one or both of $R^5$ and $R^6$ are —NO$_2$ groups. In specific embodiments, $R^6$ is a —NO$_2$ group.

In specific embodiments of formulas I-VI above, $R^{16}$ is methoxy.

In specific embodiments of formula V, $R^6$ is hydrogen or a nitro group. In specific embodiments of formula V, $R^{16}$ is hydrogen or methoxy. In specific embodiments of formula V, $R^6$ is hydrogen or a nitro group, $R^{16}$ is hydrogen or methoxy and $R^2$ is hydrogen. In specific embodiments of formula V, when $R^6$ is a nitro group, X is a halogen, particularly Cl. In specific embodiments of formula V, when $R^6$ is a nitro group, X is a pyridinium-1 yl group (see group 4, FIG. 5). In specific embodiments of formula V, when $R^6$ is a hydrogen or a nitro group, X is a group selected from groups 4-14 of FIG. 5.

β-Lactam ring systems of compounds of this invention include those of cephems (cephalosporins and cephamycins) and carbacephems. Structures of cephamycins and carbacephems are illustrated in FIG. 6. Cephamycins have a 7-methoxy group as illustrated (e.g., $R^{16}$=methoxy).

The invention provides compounds of Formula I (and II-IV) as generally described above and as more specifically described hereinafter, for use as β-lactamase inhibitors and β-lactam antibiotics. Compounds of this invention can exhibit one or both of these functions and as such are useful in a variety of human and veterinary therapeutic applications for treatment of microbial infections and complications thereof. The compounds of this invention are particularly useful for treatment of infections by microorganisms, particularly bacteria which are known to exhibit resistance to one or more β-lactam antibiotics. The compounds of this invention are useful for inhibition of the growth of microorganisms including bacteria in vivo or in vitro applications. β-Lactam inhibitors of this invention may be combined with β-lactam antibiotics to provide for inhibition of β-lactamases for in vivo or in vitro applications.

Compounds of this invention as described above in which the functionalized acetamido groups have been hydrolyzed and where R is a benzylic group are useful in the synthesis of β-lactam inhibitors and β-lactam antibiotics which exhibit β-lactamase inhibition or inactivation and in which $R^1$ group is that of a known β-lactam antibiotic. A β-lactam inhibitor which does not exhibit antibiotic activity or in which it is desired to improve antibiotic activity can be prepared from X group containing compounds of this invention by replacing the R1 group with a selected functionalized acetamide group which is found in a β-lactam antibiotic known in the art. Thus, this invention provides a method for making improved β-lactam antibiotics which exhibit β-lactamase inhibition in addition to antibiotic activity.

The invention is further related to pharmaceutical compositions comprising one or more compounds of this invention of Formula I and other formulas as described hereinafter.

The invention is also related to a method of treatment of infections and related disorders, diseases or complications by administering a therapeutically effective amount or combined amount of one or more compounds of the invention optionally in combination with a therapeutically effective amount or a combined amount of one or more known β-lactam antibiotics.

The invention is further related to a method of inhibiting the growth of microorganisms, particularly bacteria, by contacting the microorganism in vivo or in vitro with an amount of one or more of the compounds of this invention, optionally in combination with a known P-lactam antibiotic, particularly an antibiotic that has been used in the past or is currently for human or animal therapeutic applications.

DETAILED DESCRIPTION OF THE INVENTION

The invention relates to improved β-lactam antibiotics, methods of making and using the same. The compositions described herein have the ability to inhibit or inactivate one or more β-lactamase in addition to having antibacterial activity. The invention further relates to certain β-lactam compounds that inhibit or inactivate one or more β-lactamase. The invention also relates to certain β-lactam compounds that inhibit or inactivate one or more β-lactamases in addition to having antibacterial activity. The compositions described herein have the ability to inhibit or inactivate more than one β-lactamase in addition to having antibacterial activity. The invention further relates to certain β-lactam compounds that inhibit or inactivate more than one β-lactamase. The invention also relates to certain β-lactam compounds that inhibit or inactivate more than one β-lactamase in addition to having antibacterial activity. In specific embodiments, compounds of the invention broadly inhibit or inactivate more than one β-lactamase from all groups 1, 2, and 3. In specific embodiments of the invention, compounds irreversibly inhibit or inactivate one or more than one β-lactamase.

In one embodiment, the invention relates to compounds of formula I or IA:

I

Figure 4:
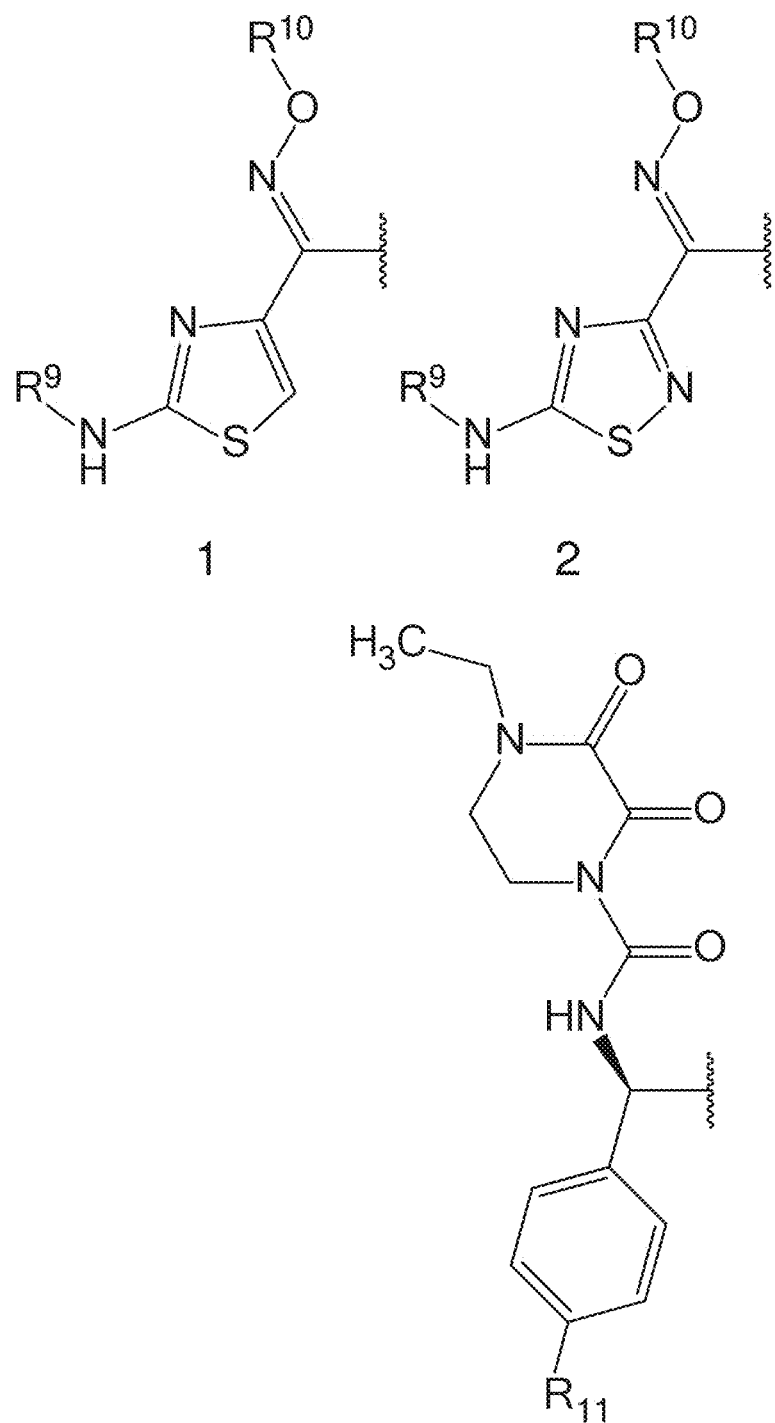
FIG. 4 depicts illustrative $R^1$ groups for compounds of Formula I.
Figure 5:
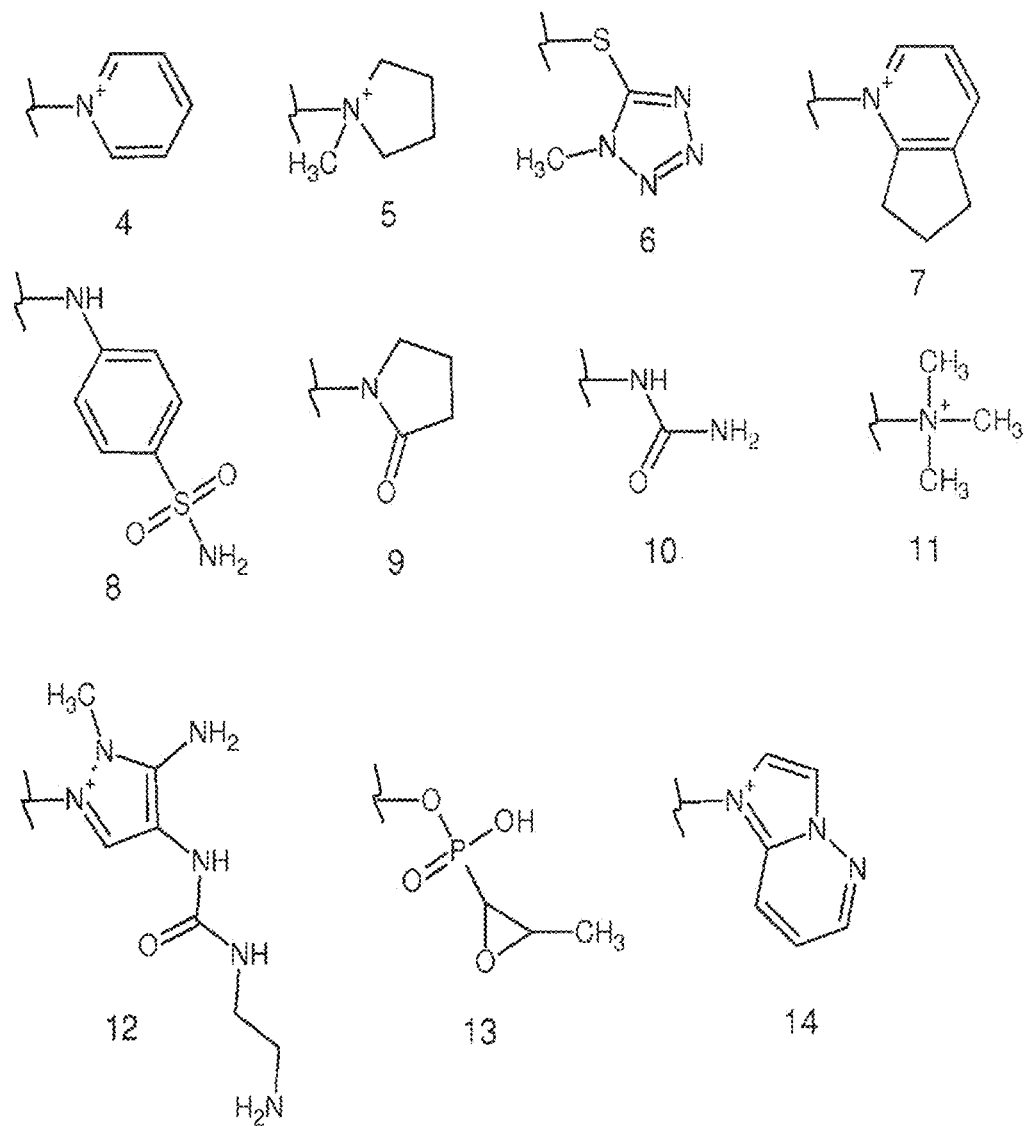
FIG. 5 depicts illustrative X leaving groups for compounds of formula I.

IA and pharmacologically acceptable salts thereof wherein:

L in formula I is —$CH_2$— or —$(CH_2=CH_2)_p$—, where p is 0 or an integer number ranging from 1 to 5 and preferably is 0 or 1;

$R^{16}$ is hydrogen or a C1-C3 alkoxy, and is preferably methoxy;

—Z— is —O—, —$CH_2$—, —S—, —SO—, or —$SO_2$—, where R' is hydrogen or $C_1$-$C_6$ alkyl;

n is an integer from 0 to 5;

$R^3$, $R^4$, $R^5$, $R^6$, $R^7$ and $R^8$ are selected from the group consisting of hydrogen, halogen, $C_1$-$C_6$ alkyl, $C_1$-$C_6$ alkoxy, $C_1$-$C_6$ alkylsulfonyl, nitro, cyano, $C_1$-$C_6$ alkylamino, $C_1$-$C_6$ dialkylamino, and $C_1$-$C_6$ trialkylammonium;

$R^2$ is hydrogen, $C_1$-$C_6$ alkyl, or $C_1$-$C_6$ alkoxy;

X is a good leaving group selected from the group consisting of halogen, $C_1$-$C_6$ esters, $C_1$-$C_6$ thioesters, $C_1$-$C_6$ alcohols, $C_1$-$C_6$ alkylamino, $C_1$-$C_6$, dialkylamino, and $C_1$-$C_6$ trialkylammonium, $C_1$-$C_6$ phosphate esters, $C_1$-$C_6$ phosphite esters, $C_1$-$C_6$ sulfate esters, $C_1$-$C_6$ sulfite esters, the groups 4-14 depicted in FIG. 5 and other leaving groups from known β-lactam antibiotics and pharmacologically acceptable salts thereof; and $R^1$ is a methylene functionalized with pharmacologically acceptable groups from known β-lactam antibiotic including groups, such as groups 1-3 depicted in FIG. 4, wherein $R^9$ is hydrogen or phosphate, $R^{10}$ is hydrogen $C_1$-$C_6$ alkyl or $C_1$-$C_6$ carboxylic acid, and $R^{11}$ is hydrogen or hydroxyl and pharmacologically acceptable salts, thereof. More specifically, $R^{10}$ is hydrogen, methyl, ethyl, —$CH_2$—COH, —$CH_2$—$CH_2$—COOH, —$C(CH_3)_2$—COOH.

As illustrated in FIG. 4, in specific embodiments, $R^1$ is a functionalized methylene group or imine group of structures:

(also called a substituted methanone O-substituted oxime).

In an additional embodiment, $R^1$ is a methanone O-substituted oxime as shown where $R^{13}$ is an optionally substituted phenyl and is more specifically an unsubstituted phenyl or a p-OH phenyl and $R^{12}$ is:

and $R_{15}$ is a $C_1$-$C_3$ alkyl group.

In specific embodiments, $R^1$ groups are benzyl groups or substituted benzyl groups. In more specific embodiments, $R^1$ groups have formula:

where $Y_1$ is —$NH_2$ or —$SO_3H$ and $Y_2$ is H or OH.

In specific embodiments, $R^1$ is a thiophen-2-ylmethyl.

As illustrated in FIG. 5, groups 4-14 are X groups useful in the compounds of the invention. Additional useful X groups include:

where each R20 independently is selected from hydrogen, C1-C3 alkyl or two adjacent $R_{20}$ together with the atoms to which they are attached form a 5-6 member carbocyclic or heterocyclic ring which may contain one or more double bonds or be aromatic. In one embodiment, all R20 are hydrogen. In another embodiment, two adjacent R20 form an unsubstituted 5-6 member carbocyclic ring;

where each $R_{21}$ independently is selected from hydrogen, C1-C3 alkyl, or two $R_{21}$ together with the atom to which they are attached form a 5-6 member heterocyclic ring. In an embodiment, one $R_{21}$ is a C1-C3 alkyl and the two remaining $R_{21}$ form together with the N to which they are attached a 5 or 6 member unsubstituted saturated heterocyclic ring. In an embodiment, all $R_{21}$ are C1-C3 alkyl groups. In an embodiment, all $R_{21}$ are methyl groups;

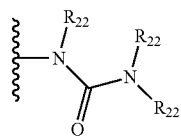

where each $R_{22}$ independently is hydrogen or a C1-C3 alkyl group or two $R_{22}$ together with the atoms to which they are attached form a 5-6 member heterocyclic ring which may be saturated, or contain one or two double bonds. In a specific embodiment, each $R_{22}$ is hydrogen. In an embodiment, one or more $R_{22}$ is a C1-C3 alkyl group.

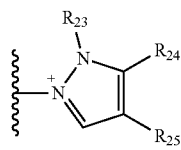

where $R_{23}$ is hydrogen or a C1-C3 alkyl, R24 is hydrogen, a C1-C3 alkyl, a —N(R$_{31}$)$_2$ group, or a —NH—CO—NHR$_{31}$ group and $R_{25}$ is hydrogen, a C1-C3 alkyl, a —N(R$_{31}$)$_2$ group, or an —NH—CO—NH—R$_{31}$ group, where $R_{31}$ is hydrogen, C1-C3 alkyl, or C1-C3 aminoalkyl, or $R_{24}$ and $R_{25}$ together with the atoms to which they are attached form a 5-6 member carbocyclic ring or heterocyclic ring (containing O, N or S) which optionally contains one or two double bonds or is aromatic. In specific embodiments, $R_{23}$ is C1-C3 alkyl, $R_{24}$ is —NH$_2$ and $R_{25}$ is —NH—CO—NH—R$_{31}$ where $R_{31}$ is an amino alkyl group;

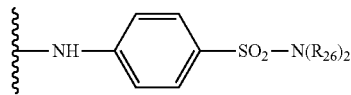

where each $R_{26}$ is independently a hydrogen or a $C_1$-$C_3$ alkyl group. In a specific embodiment, each $R_{26}$ is hydrogen;

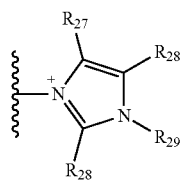

where $R_{27}$ is hydrogen or C1-C3 alkyl, each $R_{28}$ is hydrogen or a C1-C3 alkyl group, and $R_{29}$ is hydrogen, or a $C_1$-$C_3$ alkyl or $R_{27}$ with its adjacent $R_{28}$ or $R_{29}$ with one of $R_{28}$ together with the atoms to which they are attached forms a 5-6 member heterocyclic or carbocyclic ring. In a specific embodiment $R_{27}$ is hydrogen. In a specific embodiment, each $R_{27}$, $R_{28}$ and $R_{29}$ is hydrogen or a C1-C3 alkyl group. In a specific embodiment, $R_{29}$ and one of $R_{28}$ together form a 6-member heterocyclic ring. In a specific embodiment, —R$_{28}$—R$_{29}$— are —CH=CH—CH=N—;

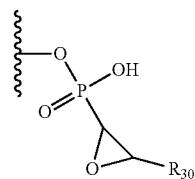

where $R_{30}$ is hydrogen or a C1-C3 alkyl group. In a specific embodiment, C30 is a C1-C3 alkyl group; or

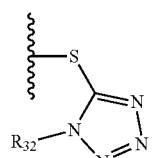

where $R_{32}$ is hydrogen or a C1-C3 alkyl group. In specific embodiments, $R_{32}$ is a C1-C3 alkyl group.

X groups include groups that carry a positive charge on the nitrogen attached to the styryl group. It will be appreciated in the art that compounds containing such groups are prepared as salts including a selected anion. In specific embodiments, the anions are pharmaceutically acceptable anions.

In specific embodiments, compounds of the invention include:

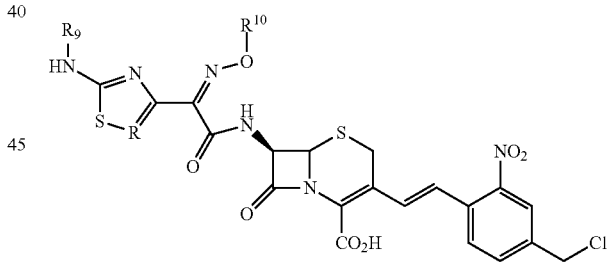

where $R^9$ is hydrogen, $R^{10}$ is hydrogen, methyl, ethyl, —CH$_2$—COH, —CH$_2$—CH$_2$—COOH, or —C(CH$_3$)$_2$—COOH, and

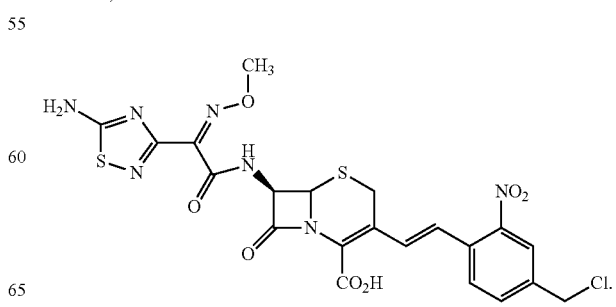

In specific embodiments, compounds of the invention include pharmaceutically acceptable salts of cations of formula:

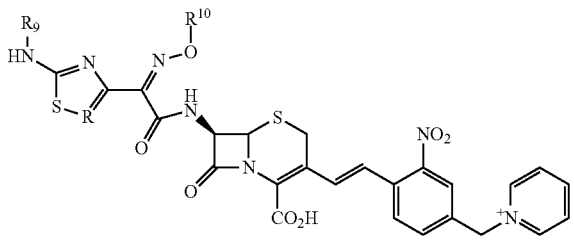

where $R^9$ is hydrogen, $R^{10}$ is hydrogen, methyl, ethyl, —$CH_2$—COH, —$CH_2$—$CH_2$—COOH, or —$C(CH_3)_2$—COOH, and

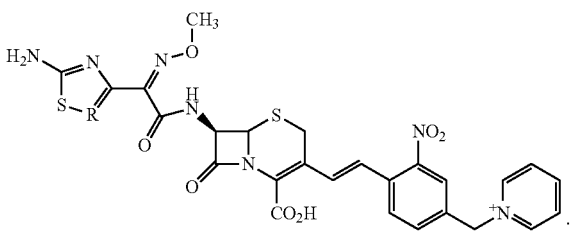

Pharmaceutically acceptable salts include halide salts (particularly chloride and bromide salts) as well as salts of organic anions, such as acetate or trifluoroacetate.

In additional related embodiments compounds of the invention include:

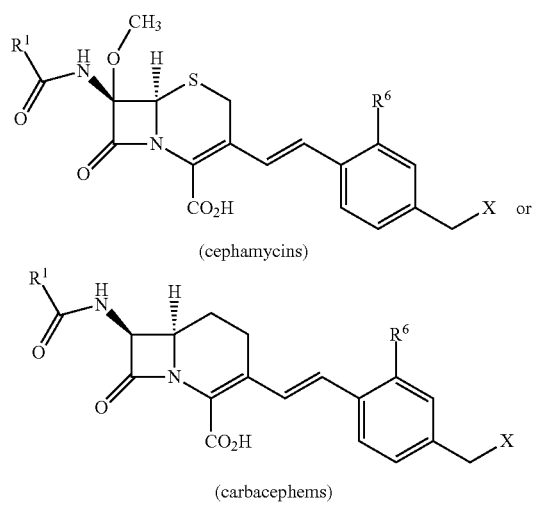

(cephamycins)

(carbacephems)

or pharmaceutically acceptable salts thereof, where R1 and X are as defined for formula 1 and $R^6$ is hydrogen of a nitro group.

The term "alkyl" refers to a monoradical of a branched or unbranched (straight-chain or linear) saturated hydrocarbon and to cycloalkyl groups having one or more rings. Unless otherwise indicated preferred alkyl groups have 1 to 22 ($C_1$-$C_{22}$) carbon atoms and more preferred are those that contain 1-12 carbon atoms ($C_1$-$C_{12}$). Short alkyl groups are those having 1 to 6 carbon atoms ($C_1$-$C_6$) and those having 1-3 carbon atoms ($C_1$-$C_3$), including methyl, ethyl, propyl, butyl, pentyl and hexyl groups, including all isomers thereof. Long alkyl groups are those having 8-30 carbon atoms and preferably those having 12-22 carbon atoms ($C_{12}$-$C_{22}$). The term "cycloalkyl" refers to cyclic alkyl groups having preferably 3 to 12 ($C_3$-$C_{12}$) carbon atoms having a single cyclic ring or multiple condensed rings. Descriptions herein with respect to alkyl groups apply generally to cycloalkyl groups. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups including cycloalkyl groups are optionally substituted as defined below.

The term "alkenyl" refers to a monoradical of a branched or unbranched unsaturated hydrocarbon group having one or more double bonds and to cycloalkenyl groups having one or more rings wherein at least one ring contains a double bond. Unless otherwise indicated alkyl groups have 2 to 22 carbon atoms ($C_{2-22}$) and more preferred are those that contain 2-12 carbon atoms ($C_2$-$C_{12}$). Alkenyl groups may contain one or more double bonds (C=C) which may be conjugated or unconjugated. Preferred alkenyl groups as substitutents are those having 1 or 2 double bonds and include omega-alkenyl groups. Alkenyl groups can contain 2-5, 4, 3, or 2 conjugated double bonds. Alkenyl groups include those having 2 to 6 carbon atoms ($C_2$-$C_6$) and those having 2-3 carbon atoms ($C_2$-$C_3$), including ethylene (vinyl), propylene, butylene, pentylene and hexylene groups including all isomers thereof. The term "cycloalkenyl" refers to cyclic alkenyl groups of from 3 to 22 carbon atoms ($C_3$-$C_{22}$) having a single cyclic ring or multiple condensed rings in which at least one ring contains a double bond (C=C). Descriptions herein with respect to alkenyl groups apply generally to cycloalkenyl groups. Cycloalkenyl groups preferably have 3-12 carbon atoms ($C_3$-$C_{12}$). Cycloalkenyl groups include, by way of example, single ring structures (monocyclic) such as cyclopropenyl, cyclobutenyl, cyclopentenyl, cyclohexenyl, cyclooctenyl, cylcooctadienyl and cyclooctatrienyl as well as multiple ring structures. Unless otherwise indicated alkenyl groups including cycloalkenyl groups are optionally substituted as defined below.

The term "alkynyl" refers to a monoradical of an unsaturated hydrocarbon having one or more triple bonds (C≡C). Unless otherwise indicated preferred alkyl groups have 2 to 22 carbon atoms and more preferred are those that contain 2-12 carbon atoms. Alkynyl groups include ethynyl, propargyl, and the like. Short alkynyl groups are those having 2 to 6 carbon atoms ($C_2$-$C_6$) and those including 2 or 3 carbon atoms ($C_2$-$C_3$), including all isomers thereof. Longer alkynyl groups are those having 6-12 carbon atoms ($C_6$-$C_{12}$). The term "cycloalkynyl" refers to cyclic alkynyl groups of from 3 to 22 ($C_3$-$C_{22}$) carbon atoms having a single cyclic ring or multiple condensed rings in which at least one ring contains a triple bond. Descriptions herein with respect to alkynyl groups apply generally to cycloalkynyl groups. Unless otherwise indicated alkynyl groups including cycloalkynyl groups are optionally substituted as defined below.

The term "aryl" refers to a chemical group containing an unsaturated aromatic carbocyclic group of from 6 to 22 carbon atoms ($C_6$-$C_{22}$) having a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). An aryl group is formally formed by removal of a hydrogen from an aryl compound. Aryls include phenyl, naphthyl and the like. Aryl groups may contain portions that are alkyl, alkenyl or akynyl in addition to the unsaturated aromatic ring(s). The term "alkaryl" refers to the aryl groups containing alkyl portions, i.e., -alkylene-aryl and -substituted alkylene-aryly. Such alkaryl groups are exemplified by benzyl, phenethyl and the like.

The term "heterocyclyl" generically refers to a monoradical that contains at least one ring of atoms, typically a 3-10 member ring, preferably a 5, 6 or 7 member ring which may be a saturated or unsaturated ring (e.g., containing double bonds) wherein the ring can contain one or more carbon atoms and one or more heteroatoms (a non-carbon atom). Heterocyclic groups can contain 1, 2 or 3 rings (2 or more rings can be designated a ring system) at least one of which is a heterocyclic ring. To satisfy valence the heteroatom may be bonded to H or a substituent group. Ring carbons may be replaced with —O—, —S—, —NR—, —N═, among others, where R in this definition is hydrogen or an alkyl, aryl, heterocyclyl or heteroaryl group. Several heterocyclic groups, rings and rings systems are more specifically described in the specification hereof.

The term "heteroaryl" refers to a group that contains at least one aromatic ring (typically a 5 or 6-member ring) in which one or more of the ring carbons is replaced with a heteroatom (non-carbon atom). To satisfy valence the heteroatom may be bonded to H or a substituent group. Ring carbons may be replaced with —O—, —S—, —NR—, —N═, among others, where R in this definition is hydrogen or an alkyl, aryl, heterocyclyl or heteroaryl group. Heteroaryl groups may include one or more aryl groups (all-carbon aromatic rings) or heteroaryl rings and aryl rings of the heteroaryl group may be linked by a single bond or a linker group (e.g., alkylene, —(CH$_2$)$_n$—, e.g., n=1-6) or may be fused. Heteroaryl groups include those having aromatic rings with 5 or 6 ring atoms of which 1-3 ring atoms are heteroatoms. Preferred heteroatoms are —O—, —S—, —NR— and —N═. Heteroaryl groups include those containing 5-12 carbon atoms. Unless otherwise noted heteroaryl groups are optionally substituted as described herein.

"Haloalkyl" refers to alkyl as defined herein substituted by one or more halo groups as defined herein, which may be the same or different. Representative haloalkyl groups include, by way of example, perfluoroalkyl groups, trifluoromethyl, difluoromethyl, chloromethyl, bromomethyl, chloro-ethyl, bromo-ethyl, chloro-cyclopropyl, 2,3-dichlorocyclopropyl, and the like. Haloalkyl groups include those having 1-6 (C$_1$-C$_6$) and 1-3 (C$_1$-C$_3$) carbon atoms and which 1, 2, 3, 5, 7, 9, 11, 13 (e.g., perchloro groups), 1-6 or 1-13 halogens. Halogens include among others, chlorine, bromine, iodine and fluorine. In celiain embodiments, chlorine, bromine and iodine are preferred halogens.

The term "haloaryl" similarly refers to an aryl group as defined herein substituted by one or more by one or more halo groups as defined herein, which may be the same or different. Representative haloaryl groups include among others para-halophenyl, ortho-halophenyl, meta-halophenyl, and phenyl rings carrying combinations of 2-5 halogens at ortho, meta, para positions or combinations thereof. Haloaryl groups include those having 6 or 12 carbon atoms (C$_6$ or C$_{12}$) which can carry 1-5 or 1-9 halogens. Haloaryls include perhalogenated aryl groups. Halogens include among others, chlorine, bromine, iodine and fluorine. In celiain embodiments, chlorine, bromine and iodine are preferred halogens.

The term alkoxy (or alkoxide) refers to a —O-alkyl group, where alkyl groups are as defined above. The term alkenoxy (alkenoxide) refers to a —O-alkenyl group where alkenyl groups are as defined above wherein the double bond can in certain embodiments be positioned at the carbon bonded to the oxygen. In most substituents that are alkeneoxy groups the double bond is preferably not positioned at the carbon bonded to the oxygen. The term alkynoxy (alkynoxide) refers to a —O-alkynyl group where alkynyl groups are as defined above and wherein a triple bond is preferably not positioned at the carbon bonded to the oxygen. The term aryloxy, refers to an —O-aryl group. The term heteroaryloxy, refers to an —O-heteroaryl group. The term heterocyclyloxy, refers to an —O-heterocyclyl group.

The term oxy refers to —O—, as for example in alkyloxy. The term oxo refers to O═, in certain instances to refer to the presence of a carbonyl group, e.g., 2-oxo-pyrrolidinyl group have the structure:

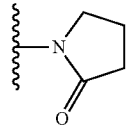 [SMILES: *N1CCCC1=O]

The term "amino" refers generically to a —N(R$_1$)$_2$ group wherein R$_1$ for this definition and independently of other R$_1$ is hydrogen, alkyl, alkenyl, alkynyl, aryl, heterocyclyl, or heteroaryl radical as described above. Two of R$_1$ may be linked to form a ring. An "alkyl amino" group refers to an amino group wherein at least one R$_1$ is alkyl. An "aryl amino" group refers to an amino group [—N(R$_1$)$_2$] wherein at least one R$_1$ is aryl.

The term "amido" refers generically to an —CO—N(R$_2$)$_2$ group wherein R$_2$, for this definition, independently of other R$_2$ is hydrogen, or an alkyl alkenyl, alkynyl, aryl, heterocyclyl, or heteroaryl radical as described above. Two of R$_2$ may be linked to form a ring. An "alkyl amido" group refers to an amido group wherein at least one R$_2$ is alkyl. An "aryl amido" group refers to an amido group wherein at least one R$_2$ is aryl.

The term "aminoacyl" group" refers generically to an —NR$_3$—CO—R$_3$ group wherein, for this definition each R$_3$ independently is hydrogen, or an alkyl, alkenyl, alkynyl, aryl, heterocyclyl, or heteroaryl radical as described above. An "alkyl aminoacyl" group refers to an aminoacyl group wherein at least one R$_3$ is alkyl. An "aryl amido" group refers to an aminoacyl group wherein at least one R$_3$ is aryl. A variety of amino acyl group are more specifically described in the specification hereof.

The term "imine" refers generically to an —N═C(R$_4$)$_2$ group or an —CR$_4$═NR$_5$ group wherein in this definition each R$_4$ and R$_5$ independently is hydrogen, or an alkyl, alkenyl, alkynyl, aryl, heterocyclyl, or heteroaryl radical as described above. Two of R$_4$ or R$_4$ and R$_5$ together may be linked to form a ring, which can be a 5-10 member ring. An "alkyl imine" group refers to an imine group wherein at least one R$_4$ or R$_5$ is alkyl. An "aryl imine" group refers to an imine group wherein at least one R$_4$ or R$_5$ is aryl. Several imine groups are more specifically described in the specification hereof.

The term "sulfenyl" refers to the radical —S—R$_6$ where R$_6$, in this definition, is an alkyl, alkenyl, alkynyl, aryl, heterocyclyl, or heteroaryl radical as described above. The term thio refers to the —S— moiety. The radical —S—R$_6$ can also be called R$_6$-thio, e.g., alkylthio, alkenyl thio and the like.

The term "sulfhydryl" refers to the —SH group.

The term "sulfonyl" refers to the radical-SO$_2$—R$_7$ where R$_7$, in this definition, is an alkyl, alkenyl, alkynyl, aryl, heterocyclyl, or heteroaryl radical as described above.

The term "sulfonate" refers to the radical-SO$_3$—R$_8$ where R$_8$, in this definition, is hydrogen, alkyl, alkenyl, alkynyl, aryl, heterocyclyl, or heteroaryl radical as described above. An "alkyl sulfonate" group refers to a sulfonate group wherein R$_8$ is alkyl. An "aryl sulfonate" group refers to an sulfonate group wherein is R$_8$ is aryl. The group —SO$_3$H can be in the ionic form —SO$_3^-$. Alkyl, alkenyl, alkynyl, aryl, heteroaryl, and heterocyclic groups or the alkyl, alkenyl, alkynyl, aryl, heteroaryl, and heterocyclic positions of groups are optionally substituted (unless noted otherwise) as described herein and may contain 1-8 non-hydrogen substituents dependent upon the number of carbon atoms in the group and the degree of unsaturation of the group. Alkyl, alkenyl, alkynyl, aryl, heteroaryl, and heterocyclic groups may also be unsubstituted.

Optional substitution refers to substitution with one or more of the following functional groups (hydrogen is not herein considered to be a functional group): Halogens, hydroxyl (—OH), —CN, —SH, alkyl, alkenyl, alkynyl, aryl, heterocyclyl, heteroaryl, alkoxy, alkenoxy, alkynoxy, aryloxy, heteroaryloxy, heterocyclyloxy, sulfenyl, sulfonyl, sulfonate, amine, amido, aminoacyl, imine, —COR$_9$, —COOR$_9$, —CON(R$_9$)$_2$, —OCOR$_9$, —OCON(R$_9$)$_2$, haloalkyl, haloalkenyl, haloaryl, —CO—C(R$_9$)$_2$—CO—, —NR$_9$COR$_9$, —NR$_9$COOR$_9$, —COO$^-$ C$^+$ (carboxylate salt) or —NR$_9$CON(R$_9$)$_2$, where each R$_9$ in this definition is selected from hydrogen, alkyl, alkenyl, alkynyl, aryl, heterocyclyl, heteroaryl, (which in turn are optionally substituted) and C$^-$ is a pharmaceutically acceptable cation (of a pharmaceutically acceptable salt).

As to any of the above groups which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Compounds of the invention include those having 1, 2, 3, 4, 5 or 6 of such substituents.

The invention also relates to prodrug forms of the compounds of Formula I, II or III. The term "prodrug" refers to an agent that is converted into the parent drug in vivo. A prodrug is metabolized or otherwise converted to the biologically, pharmaceutically, or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug, or to alter other characteristics or properties of a drug. Prodrugs may be easier to administer than the parent drug in some situations. For example, the prodrug may be bioavailable by oral administration but the parent drug is not, or the prodrug may improve solubility to allow for intravenous administration.

Knowledge of the pharmacodynamics processes and drug metabolism in vivo allows those of ordinary skill in the art, once a pharmaceutically active compound is known, can design prodrugs of the compound. Various forms of prodrugs are well known in the art. For example of such prodrug derivatives see Design of Prodrugs, edited by H. Bundgaard, (Elsevier, 1985; Methods in Enzymology, Vol. 42, at pp. 309-396, edited by K. Widder et al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191 (1991); H. Bundgaard, Advanced Drug Delivery Review, Vol. 8, p. 1-38 (1992); H. Bundgaard et al. Journal of Pharmaceutical Sciences, Vol. 77, p. 285 (1988); and Nogrady (1985) Medicinal Chemistry A Biochemical Approach, Oxford University Press, New York, pp. 388-392.

The compounds of this invention may contain one or more chiral centers. Accordingly this invention is intended to include racemic mixtures, diastereomers, enantiomers, and mixtures enriched in one or more stereoisomers. The scope of the invention as described and claimed encompasses the racemic forms of the compounds as well as the individual enantiomers and non-racemic mixtures thereof.

Salts of compounds of the present invention are also within the scope of this invention. Reference to the compound formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety, such as, but not limited to an amine or a pyridine ring, and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, berates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sultanates (such as those mentioned herein), tmirates, thiocyanates, toluenesulfonates such as tosylates, undecanoates, and the like.

Exemplary basic salts include ammonium salts, alkali metal salts, such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro abietyl)ethylenediamine], N-methyl-O-glucamines, N-methyl-O-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers or E and Z isomers (structural isomers) and/or may contain one or more chiral centers and therefore exist in enantiomeric and diastereomeric forms. The invention includes all such isomers, as well as mixtures of cis and trans isomers or E and Z isomers, mixtures of diastereomers and racemic mixtures of enantiomers (optical isomers). When no specific mention is made of the configuration (cis, trans/E, Z or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Leaving groups are typically substituents which are able to leave as a stable, weakly basic species. In some cases, leaving groups leave as anions, in other cases they leave as neutral molecules. A "good leaving group" can be recognized as being the conjugate base of a strong acid. Good leaving groups include, among others, halogens, particularly I, Br, and Cl; —CO—O—$R_{10}$; —SC(O)$R_{10}$; —OCOR$_{10}$; thiol (—SH); sulfenyl (—SR$_{10}$); phenoxy; pentafluorophenoxy; tosyl and tosyl variants including p-fluorotosyl, p-bromotosyl, p-nitrobenzyltosyl, pentafluorotosyl; or pyridinium or substituted pyridinium groups, where $R_{10}$ for this definition are selected from optionally substituted alkyl and aryl groups, specific $R_{10}$ include $C_1$-$C_3$ alkyls, particularly methyl groups.

Figure 6:
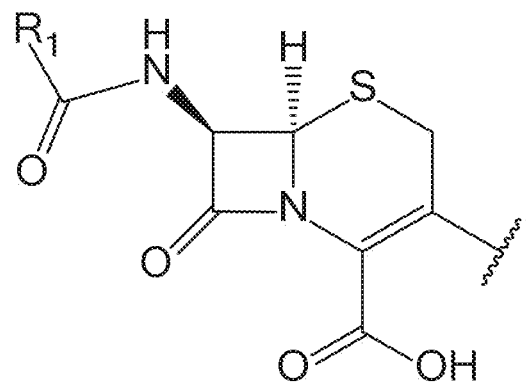
FIG. 6 depicts core structures of cephalosporins, cephamycins and carbacephems.
Figure 6:
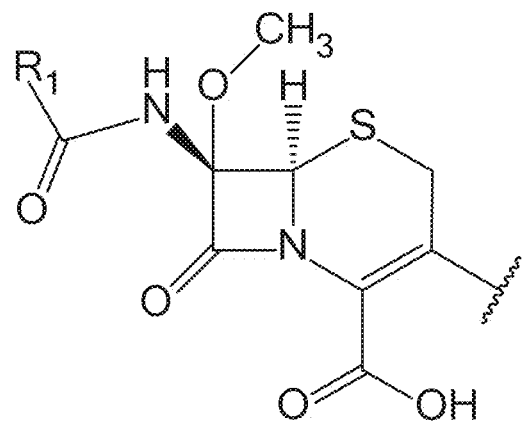
Figure 6:
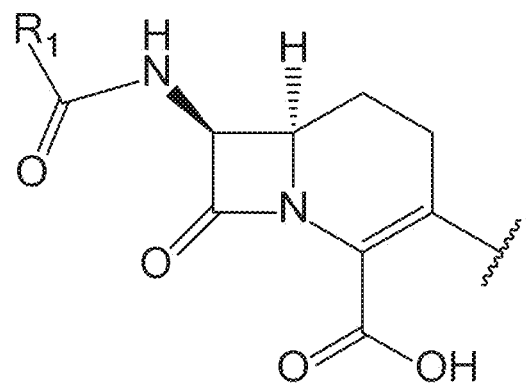

The term β-lactam antibiotic is used broadly herein to refer to any compound recognized in the art as containing a β-lactam ring structure, including for example those ring structures illustrated in FIG. 6, and which exhibits antibiotic activity against one or more microorganisms, particularly bacteria. β-lactam antibiotics include those described in the following references: Queener et al. β-lactam Antibiotics for Clinical Use 1986 (Informa Health Care); and Mitsuhashi β-lactam Antibiotics, 1981 (Japan Scientific Societies Press).

A β-lactam compound is most generally a compound which comprises a β-lactam ring. β-lactam compounds of interest in this invention are those which exhibit antibiotic activity and/or inhibition of one or more β-lactamases and preferably those that exhibit both activities.

The term β-lactamases is used broadly herein to refer to enzymes from any sources which catalyze β-lactam ring opening. β-lactamases (EC 3.5.2.6) are enzymes most commonly produced by bacteria. β-lactamases catalyze the hydrolytic ring opening of β-lactam rings and are responsible for conferring bacterial resistance to β-lactam antibiotics such as penicillins, penams, penems, cephems, cephalosporins, carbacephems, cephamycins, and monobactams. Some β-lactamases have evolved to thermodynamic perfection wherein diffusion of β-lactam to β-lactamase is the rate determining step. Many different classification systems have been used to categorize β-lactamases including genetic and mechanistic schemes. At the simplest level β-lactamases can be divided into two categories. Serine hydrolases catalyze their reactions through the use of an active site serine that is acylated during the reaction in a Ping-Pong-Bi-Bi mechanism, if water is accounted as a substrate, or Uni-Bi-Bi, if the solvent water molecules are ignored. Metallo β-lactamases catalyze hydrolysis of the amide bond of the β-lactam ring via direct nucleophilic attack of a water molecule using one or two $Zn^{2+}$ ions. This Bi-Bi mechanism, if water is counted, or Uni-Bi mechanism, if water is ignored, does not proceed through an acyl enzyme intermediate.

β-Lactamase inhibitor is also used broadly herein to refer to chemical species, particularly small molecules (e.g., molecules other than peptides or proteins). β-lactamases can be inhibited by small molecules via reversible competitive, noncompetitive, uncompetitive, and slow tight binding mechanisms as well as irreversible active-site-directed and mechanism based or suicide mechanisms. Such inhibitor molecules decrease the catalytic rate of B-lactamase reactions or completely prevent β-lactamases from performing any catalysis at all. Examples of reversible competitive inhibitors include boronic acids. Examples of active-site-directed irreversible inhibitors include phosphate or phosphonate esters. Examples of mechanism based inhibitors include clavulanic acid, sulbactam and tazobactam.

β-Lactam compounds of interest in this invention are those which exhibit inhibition of one or more β-lactamases and preferably those that exhibit both activities and/or antibiotic activity. β-lactamase inhibitors of this invention do not include clavulanic acid, sulbactam and tazobactam, however, one or more compounds of this invention can be combined with one or more of these known β-lactamase inhibitors in pharmaceutical compositions or medicaments.

Compounds of this invention can be synthesized employing methods as described herein or using routine adaptations of these methods with art-known or commercially available starting materials and reagents in view of what is generally known in the art with respect to the synthesis of the various classes of known β-lactam inhibitors and known β-lactam antibiotics. For example, synthesis of starting materials for synthesis of compounds of the invention and also in the synthesis of compounds of the invention may be achieved using well-known methods and readily available materials, such as provided in March; Larock, *Comprehensive Organic Transformations* (VCH Publishers, 1989); Larock *Comprehensive Organic Transformations: A Guide to Functional Group Preparations*. Second Edition, (John Wiley & Sons, Inc., 1999); Smith, March March's *Advanced Organic Chemistry: Reactions, Mechanisms, and Structure*. Sixth Edition, (John Wiley & Sons, Inc., 2007); G. I. Georg, *The Organic Chemistry Of* β-Lactams. (VCH 1992), Page *Chemistry of* β-*Lactams* (Springer. 1992); Smith, Smith *Organic Synthesis*. Second Edition (McGraw-Hill Science/Engineering/Math, 2001); Bruggink A, *Synthesis of* [β-*lactam Antibiotics: Chemistry. Biocatalysis*& *Process Integration* (Springer, 2001.) U.S. published patent application 2009/0131394 provides additional details of synthesis of β-lactam compounds which can be useful in preparation of compounds of this invention. This application is incorporated by reference herein in its entirety for descriptions of β-lactam compounds therein and for descriptions of synthetic methods.

Compounds of this invention, for example those with benzyl groups as the $R^1$ groups in formulas herein, can be used as intermediates in the synthesis of β-lactam compounds having various aminoacyl groups at this ring position. For example, modification of the aminoacyl groups at the 7 position (or equivalent position) on the core ring system can be accomplished by those of ordinary skill in the art using art-recognized techniques, starting materials and reagents which are available commercially or by application of art-known synthetic methods. Removal of a phenylacetyl group (benzyl-CO—) can be accomplished, for example, by deamidation through one of several methods including the use of $PCl_5$, penicillin amidase, cephalosporin C amidase or penicillin acylase to give the free amine at the 7 position (or equivalent position). The amino group can then be modified by reacting a functionalized carboxylic acid in the presence of penicillin amidase under acidic conditions or by activating the functionalized carboxylic acid with an activating agent such as cyclohexylcarbodiimide.

Mechanisms of β-lactamase inhibition. Without wishing to be bound by any particular mechanism of action of the compounds herein, the following mechanistic discussion is provided to present the current view of the inventors with respect to the inhibition of β-lactamases by compounds of this invention. It is believed that highly reactive electrophilic or nucleophilic sites (e.g., chemical moieties or groups) are generated in compounds of this invention upon opening of the lactam ring, particularly by one or more p-lactamases. The species generated on lactam ring opening are generated from certain latent reactive moieties or groups which are conjugated to the β-lactam ring in the compounds of this invention. These sites are believed capable of covalently binding to a β-lactamase enzyme nucleophile or electrophile, respectively.

The compounds of this invention are typically administered to a patient in the form of a pharmaceutical composition. Accordingly, this invention provides pharmaceutical compositions comprising a pharmaceutically-acceptable carrier or excipient and a therapeutically effective amount of a compound of formula I-III or a pharmaceutically acceptable salt thereof. The choice of a particular carrier or excipient, or combinations of carriers or excipients, will depend on the mode of administration being used to treat a particular patient or type of bacterial infection. The preparation of a suitable pharmaceutical composition for a particular mode of administration, such as oral, topical, inhaled, or parenteral administration, is well within the knowledge of those of ordinary skill in the pharmaceutical arts. Additionally, the ingredients for such compositions are commercially-available. For example, conventional formulations and formulations techniques are described in Remington's Pharmaceutical Sciences. 17th Ed. (Mace Publishing Co., 1985) and Banker, Rhodes (Eds) *Modern Pharmaceutics* 4th Edition (Marcel Dekker, Inc, 2002).

The pharmaceutical compositions of this invention will typically contain a therapeutically effective amount of a compound or a pharmaceutically acceptable salt thereof. The pharmaceutical compositions of this invention can contain a combined therapeutically effective amount of two or more compounds or pharmaceutically-acceptable salts thereof. The pharmaceutical compositions of this invention can contain a combined therapeutically effective amount of one or more compounds or pharmaceutically-acceptable salts thereof, in combination with one or more known β-lactam antibiotics. Typically, such pharmaceutical compositions will contain from about 0.01 to about 99.99%, from about 0.1 to about 99.9%, from about 1% to 99%, from about 5% to about 95%, from about 10% to about 10% or from about 10% to about 50% of the active agent(s) of this invention. One of ordinary skill in the art knows or can readily determine therapeutically effective amounts of known β-lactam antibiotics. Compounds of this invention can exhibit antibiotic activity and/or β-lactamase inhibition. The amount or combined therapeutically effective amount of a compound of this invention for antibiotic effect may be different from that for β-lactamase inhibition. One of ordinary skill in the art can determine therapeutically effective amounts of the compounds of this invention employing art-known techniques without undue experimentation. In pharmaceutical compositions in which a β-lactamase inhibitor of this invention is combined with a known-lactamase antibiotic or a β-lactamase antibiotic of this invention, the therapeutically effective amount typically employed will be that for achieving β-lactamase inhibition.

Pharmaceutical compositions of this invention include those suitable for parenteral administration, particularly intravenous administration. Such pharmaceutical compositions typically comprise a sterile, physiologically-acceptable aqueous solution containing a therapeutically effective amount or combined amount of a compound or pharmaceutically-acceptable salts thereof. Physiologically-acceptable aqueous carrier solutions suitable for intravenous administration of active agents are well-known in the art. Such aqueous solutions include among others, 5% dextrose, Ringer's solutions (lactated Ringer's injection, lactated Ringer's plus 5% dextrose injection, acylated Ringer's injection), Normosoi-M, lsolyte E and the like. Optionally, such aqueous solutions may contain a co-solvent, for example, polyethylene glycol; a chelating agent, for example, ethylenediamine tetracetic acid; a solubilizing agent, for example, a cyclodextrin; an anti-oxidant, for example, sodium metabisulphite; and the like.

The aqueous pharmaceutical compositions of this invention can be lyophilized and subsequently reconstituted with a suitable carrier prior to administration. The carrier in this composition comprises, for example, sucrose, mannitol, dextrose, dextran, lactose or a combination thereof.

Pharmaceutical compositions of this invention include those for oral administration in which the active ingredient is combined with a solid carrier or excipient. Choice of carriers and excipients for oral dosage forms is within the knowledge of one of ordinary skill the art.

The pharmaceutical compositions of this invention can be packaged in a unit dosage form. This term refers to a physically discrete unit suitable for dosing a patient, i.e., each unit containing a predetermined quantity of active agent calculated to produce the desired therapeutic effect either alone or in combination with one or more additional units. Unit dosage forms include, among others, tablets, capsules, solutions, suspensions, elixirs, syrups, cream, lotions, ointments, sprays and aerosols. For example, such unit dosage forms may be packaged in sterile, bottles, vials, tubes, sprayers, aerosole dispensers, sealed ampoules and the like.

Compounds of the invention are useful as antibiotics. For example. The compounds of this invention are useful for treating or preventing bacterial infections and other bacteria-related medical conditions in mammals, including humans and non-human animals (i.e., dogs, cats, horses, cows, pigs, etc.) which are caused by microorganisms susceptible to the compounds of this invention. This invention provides a method of treating a bacterial infection in a mammal, the method comprising administering to a mammal in need of treatment, a pharmaceutical composition comprising a pharmaceutically-acceptable carrier and a therapeutically effective amount or combined therapeutically effective amount of one or more compounds or pharmaceutically-acceptable salts thereof.

Compounds of the invention are useful as components of antibiotic compositions. For example, the compounds of this invention are useful in combination with known β-lactam antibiotics for treating or preventing bacterial infections and other bacteria-related medical conditions in mammals, including humans and animals (i.e., dogs, cats, horses, cows, pigs, etc.) which are caused by microorganisms susceptible to the compounds of this invention. This invention provides a method of treating a bacterial infection in a mammal, the method comprising administering to a mammal in need of treatment, a pharmaceutical composition comprising a pharmaceutically-acceptable carrier and a combined therapeutically effective amount of a known β-lactam antibiotic, including a β-lactam antibiotic of this invention and one or more β-lactamase inhibitors of formulas I-III, or pharmaceutically-acceptable salts thereof.

Compounds of this invention are useful for treating or preventing infections caused by Gram-positive bacteria and related microorganisms. For example, the compounds of this invention are effective for treating or preventing infections caused by certain *Enterococcus* spp.; *Staphylococcus* spp., including coagulase negative *Staphylococci* (CNS); *Streptococcus* spp.; *Listeria* spp.; *Clostridium* ssp.; *Bacillus* spp.; and the like. Examples of bacterial species effectively treated with the compounds of this invention include, but are not limited to, methicillin-resistant *Staphylococcus aureus* (MRSA); methicillin-susceptible *Staphylococcus aureus* (MSSA); glycopeptide intermediate-susceptible *Staphylococcus aureus* (GISA); methicmin-resistant *Staphylococcus epidennitis* (MRSE); methicillin-sensitive *Staphylococcus epidennitis* (MSSE); vancomycin-sensitive *Enterococcus faecalis* (EFSVS); vancomycin-sensitive *Enterococcus faecium* (EFMVS); penicillin-resistant *Streptococcus pneumoniae* (PRSP); *Streptococcus pyogenes; Bacillus anthracis* and the like.

Compounds of this invention are useful for treating or preventing infections caused by Gram-negative bacteria and related microorganisms. For example, the compounds of this invention are effective for treating or preventing infections cause by certain *Escherichia* spp.; *Salmonella* spp.; *Neisseria* spp.; *Helicobacter* spp.; and the like. Examples of bacterial species effectively treated with the compounds of this invention include, but are not limited to *Escherichia coli* 0157:H7; *Klebsiella pneumoniae; Salmonella enterica; Salmonella typhi; Shigella dysenteriae; Yersinia pestis; Pseudomonas aeruginosa; Vibrio cholerae; Bordetalla pertussis; Haemophilus influenzae; Helicobacter pylori; Helicobacter fells; Campylobacter jejuni; Neisseria gonorrhoeae; Neisseria meningitidis; Brucella abortus; Bacteroides fragilis; Acenitobater baumanni* and the like.

Compounds of this invention are also useful for treating or preventing infections caused by bacteria not traditionally categorized by Gram stain including, but not limited to, *Treponema pallidum; Borrelia burgdmferi; Rickettisas* spp.; and the like.

Exemplary types of infections or bacteria-related medical conditions which can be treated or prevented with the compounds of this invention include, but are not limited to, skin and skin structure infections, urinary tract infections, pneumonia, endocarditis, catheter-related blood stream infections, osteomyelitis, and the like. In treating such conditions, the patient may already be infected with the microorganism to be treated, be suspected of being infected with the microorganism or merely be susceptible to infection in which case the active agent is administered prophylactically.

The compounds of this invention are typically administered in a therapeutically effective amount by any acceptable route of administration. The compounds may be administered in a single daily dose or in multiple doses per day. The treatment regimen may require administration over extended periods of time, for example, for several days or for one to six weeks or longer. The amount of active agent administered per dose or the total amount administered will typically be determined by the patient's physician and will depend on such factors as the nature and severity of the infection, the age, weight and general health of the patient, the tolerance of the patient to the active agent, the microorganism(s) causing the infection, the route of administration and the like. Typical dosage ranges for β-lactam antibiotics are 100 mg to several grams.

Additionally, the compounds of this invention are generally effective for inhibiting the growth of bacteria. In this embodiment, bacteria are contacted either in vitro or in vivo with a growth-inhibiting amount of a compound of formula I-III or pharmaceutically-acceptable salts thereof. Inhibition of bacterial growth is typically evidenced by a decrease or lack of reproduction by the bacteria and/or by lysis of the bacteria, i.e., by a decrease in colony-forming units in a given volume over a given period of time (i.e., per hour) compared to untreated bacteria. Compounds of this invention may be baceteriostatic or bacteriocidal. Typical concentrations of -lactam antibiotics effective for bacterial growth inhibition rang from tenths of micrograms to tens of micrograms per mL.

Additionally, the compounds of this invention are generally effective for inhibiting β-lactamases. In this embodiment, the β-lactamase is contacted in vitro or in vivo with an inhibiting amount of a compound of formula I-III or pharmaceutically acceptable salts thereof. Typical effective concentrations of β-lactam inhibitors for inhibiting β-lactamases range from tenths of micrograms to tens of micrograms per mL.

The compounds of this invention can also inhibit cell wall biosynthesis in bacteria. In this embodiment, bacterial are contacted either in vitro or in vivo with a cell wall biosynthesis-inhibiting amount of a compound of formula I (or formula II or III) or a pharmaceutically acceptable salt thereof. Typical effective concentrations of β-lactam inhibitors for inhibiting cell wall biosynthesis range from tenths of micrograms to tens of micrograms per mL.

This invention additionally relates to the use of one or more compounds of this invention in the manufacture of a medicament for treatment of microbial infection, particularly bacterial infections and particularly infection of bacterial which exhibit resistance to one or more -lactam antibiotics because of the presence of β-lactamases. The medicaments comprise therapeutically effective amounts or combined amounts of one or more compounds of this invention, particularly those compounds which exhibit microbial and/or bacterial inhibition. More specifically, the invention relates to the use of one or more compounds of the formulas herein in the manufacture of a medicament for treatment of such microbial and bacterial infections. In specific embodiments the medicament manufactured is in suitable dosage form for oral, optical, parenteral, or other form suitable form of administration as a tablet, capsule, solution, cream ointment, or other suitable dosage for. In specific embodiments, the medicament further comprises a pharmaceutically acceptable carrier, excipient, or diluent and particularly a carrier or diluent suitable for oral or parenteral administration.

This invention further relates to the use of one or more compounds of this invention as β-lactamase inhibitors in the manufacture of a medicament for treatment of microbial infection, particularly bacterial infections and particularly infection of bacterial which exhibit resistance to one or more β-lactam antibiotics because of the presence of β-lactamases. In this embodiment, the medicament further comprises a therapeutically effective amount of a β-lactam antibiotic. More specifically, the invention relates to the use of one or more compounds of the formulas herein in the manufacture of a medicament for treatment of such microbial and bacterial infections. In specific embodiments the medicament manufactured is in suitable dosage form for oral, optical, parenteral, or other form suitable form of administration as a tablet, capsule, solution, cream ointment, or other suitable dosage for. In specific embodiments, the medicament further comprises a pharmaceutically acceptable carrier, excipient, or diluent and particularly a carrier or diluent suitable for oral or parenteral administration.

In specific embodiments, the invention provides the use of one or more compounds of this invention in the manufacture of a medicament for treatment of microbial infection, particularly bacterial infections and particularly infection of bacterial which exhibit resistance to one or moreβ-lactam antibiotics because of the presence of β-lactamases. In specific embodiments the medicament manufactured is in an oral or parenteral dosage form such as tablet, capsule or solution. In specific embodiments, the medicament further comprises a pharmaceutically acceptable carrier or diluent and particularly a carrier or diluent suitable for oral or parenteral administration.

Without wishing to be bound by any particular theory, there can be discussion herein of beliefs or understandings of underlying principles and mechanisms of action relating to the invention. It is recognized that regardless of the ultimate correctness of any mechanistic explanation or hypothesis, an embodiment of the invention can nonetheless be operative and useful.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group members are intended to be individually included in the disclosure. A number of specific groups of variable definitions have been described herein. It is intended that all combinations and subcombinations of the specific groups of variable definitions are individually included in this disclosure. Any compound individually named herein can be excluded from the claims. Specific names of compounds are intended to be exemplary, as it is known that one of ordinary skill in the art can name the same compounds differently.

Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers (or E/Z isomers); R/S enantiomers) of the compound described individual or in any combination.

Additionally, unless otherwise specified, all isotopic variants of compounds disclosed herein are intended to be encompassed by the disclosure. For example, it will be understood that any one or more hydrogens in a molecule disclosed can be replaced at least in part with deuterium or tritium. Similarly any one or more $^{12}C$ can be replaced, at least in part, with $^{13}C$. Isotopic variants of a molecule are generally useful as standards in assays for the molecule and in chemical and biological research related to the molecule or its use. Isotopic variants, including those carrying radioisotopes, may also be useful in biological research, diagnostic assays and in therapeutics. Methods for making such isotopic variants are known in the art.

Molecules disclosed herein may contain one or more ionizable groups [groups from which a proton can be removed (e.g., —COOH) or to which a proton may be added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

One of ordinary skill in the art will appreciate that synthetic methods, starting materials, reagents, β-lactamases, β-lactam antibiotics, commercially available β-lactam antibiotics, enzyme assays, β-lactamase activity assays, pharmaceutical formulations and dosage forms, other than those specifically exemplified can be employed in the practice of the invention without resort to undue experimentation. All art-known functional equivalents, of any such assay methods, starting materials, synthetic methods, starting materials, reagents, β-lactamases, β-lactam antibiotics, commercially available β-lactam antibiotics, enzyme assays, β-lactamase activity assays, pharmaceutical formulations and dosage forms are intended to be included in this invention.

Whenever a range is given in the specification, for example, a range of numbers of elements in a chemical group or moiety (e.g., a range of numbers of carbons, e.g., $C_1$-$C_3$), a range of any integer, a range of any number of substituents, a temperature range, a time range, or a composition range, all intermediate ranges and subranges, as well as all individual values included in the ranges given are intended to be included in the disclosure. It will be understood that any subranges or individual value or values in a range or subrange that are included in the description can be excluded from the claims herein.

As used herein, "comprising" is synonymous with "including," "containing," or "characterized by," and is inclusive or open-ended and does not exclude additional, unrecited elements or method steps. As used herein, "consisting of excludes any element, step, or ingredient not specified in the claim element. As used herein, "consisting essentially of" does not exclude materials or steps that do not materially affect the basic and novel characteristics of the claim. In an embodiment pharmaceutical compositions herein are employed for inhibiting the growth of bacteria, for treating infections and for inhibiting β-lactamases and consist essentially of one or more compounds of the invention which provide this function. Additional compositions of the invention consist essentially of one or more compounds of the invention in combination with one or more art known β-lactam antibiotics or art known β-lactamase inhibitors. It will be appreciated that a wide variety of additives may be added to the compositions of this invention, such additives may facilitate or enhance administration, shelf-life or other useful properties. Any recitation herein of the broad term "comprising", particularly in a description of components of a composition or in a description of elements of a device, is intended to encompass and describe the terms "consisting essentially of" or "consisting of". The invention illustratively described herein suitably may be practiced in the absence of any element or elements, limitation or limitations which is not specifically disclosed herein.

Although the description herein contains many specifics, these should not be construed as limiting the scope of the invention, but as merely providing illustrations of some of the embodiments of the invention. All references cited herein, other than patent documents to which priority is claimed, are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All patents and publications mentioned in the specification are indicative of the level of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compounds are claimed, it should be understood that compounds known and available in the art prior to Applicant's invention, including compounds for which an enabling disclosure is provided in the references cited herein, can be excluded included in the compound claims herein. Some references provided herein are incorporated by reference to provide details concerning synthetic methods, starting materials, reagents, known β-lactam antibiotics, pharmaceutical formulations and components of such formulations, methods of administration of such pharmaceutical composition, purification methods, and methods of analysis; as well as additional uses of the invention.

EXAMPLES

Assay for β-Lactamase Activity

A chromogenic cephalosporin, Chromacef, is synthesized and isolated as described by Yu, et al. (Yu S; Vosbeek, A; Corbella, K; Severson, J; Schesser, J; and Sutton, L D. *A chromogenic cephalosporin for β-lactamase inhibitor screening assays* (2012) Analytical Biochemistry, 438, 96-98) and used to monitor β-lactamase activity. β-Lactamase enzymes are isolated from bacteria by methods known to those knowledgeable in the art. A typical assay monitors the hydrolysis of Chromacef via the formation of a species which absorbs maximally at 442 nm (molar extinction coefficient=14,500). Absorption is monitored as a function of time in buffer (either 50 mM, pH 7.0 sodium phosphate or 100 mM, pH 7.0 Trisma buffer supplemented with 100 µM $ZnCl_2$), 100-300 µM Chromacef and 1-3 volume percent DMSO cosolvent at 30° C. using a spectrophotometer having thermal-regulated cuvette holder. The assay is initiated by addition and mixing of an appropriate amount of β-lactamase.

Assay For Time-Dependent β-Lactamase Inhibition

The 100% activity control is performed as described above using 300 µM Chromacef, 3 volume percent DMSO cosolvent in buffer (either 50 mM, pH 7.0 sodium phosphate or 100 mM, pH 7.0 Trisma buffer supplemented with 100 µM $ZnCl_2$) at 30° C. The reaction is initiated by addition and mixing of an appropriate amount of β-lactamase and the formation of product is followed as a function of time by monitoring the increase in absorbance at 442 nm as a function of time. The reaction is followed through <10% completeness and the initial rate determined via linear least squares analysis where the slope is the initial rate.

Inhibition due to competitive binding of the inhibitor at the enzyme's active site assay is performed in 300 µM Chromacef, 50-500 µM inhibitor cephalosporin, 3-5 volume percent DMSO cosolvent in buffer (either 50 mM, pH 7.0 sodium phosphate or 100 mM, pH 7.0 Trisma buffer supplemented with 100 µM $ZnCl_2$) at 30° C. The reaction is initiated by addition and mixing of the same amount of β-lactamase as used in the control reaction and the formation of product is followed as a function of time by monitoring the increase in absorbance at 442 nm as a function of time. The reaction is followed through <10% completeness and the initial rate determined via linear least squares analysis where the slope is the initial rate.

Figure 1:
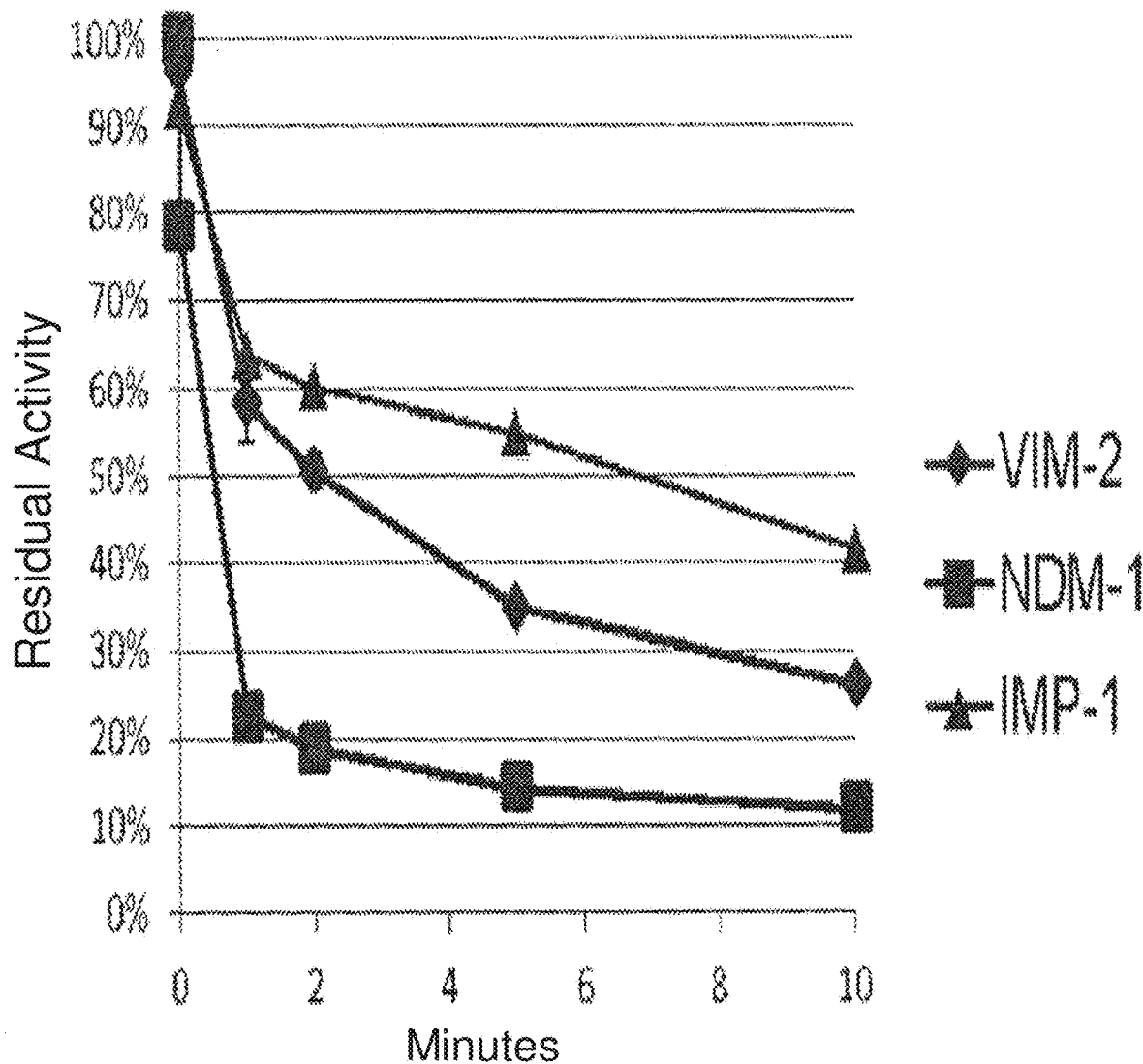
FIG. 1 shows the graph of the time-dependent inhibition or inactivation of VIM-2, NDM-1, and IMP-1 group 3a metallo-β-lactamases by compound II Cl/benzyl.

Time dependent inhibition assays are performed as described above using 50-500 µM inhibitor cephalosporin, 0.5-5 volume percent DMSO cosolvent, and the same amount of enzyme as used in the control assay in buffer (either 50 mM, pH 7.0 sodium phosphate or 100 mM, pH 7.0 Trisma buffer supplemented with 100 µM $ZnCl_2$) at 30° C. The reaction is initiated at various time points by the addition and mixing of an appropriate amount of Chromacef to give a 300 µM concentration and the formation of product is followed as a function of time by monitoring the increase in absorbance at 442 nm as a function of time. The reaction is followed through <10% completeness and the initial rate determined via linear least squares analysis where the slope is the initial rate. Representative results for the 3-(4-(chloromethyl)styryl)-7-(2-phenylacetamido)-ceph-3-em-4-carboxylic acid inhibition (compound of Formula II Cl/benzyl) of the metallo-β-lactamases, VIM-2, NDM-1, and IMP-1, are presented in FIG. 1.

Assay for Determining $IC_{50}$ Values

The 100% activity control is performed as described above using 300 µM Chromacef, 3 volume percent DMSO cosolvent in buffer (either 50 mM, pH 7.0 sodium phosphate or 100 mM, pH 7.0 Trisma buffer supplemented with 100 µM $ZnCl_2$) at 30° C. The reaction is initiated by addition and mixing of an appropriate amount of β-lactamase and the formation of product is followed as a function of time by monitoring the increase in absorbance at 442 nm as a function of time. The reaction is followed through <10% completeness and the initial rate determined via linear least squares analysis where the slope is the initial rate.

Ten-minute inhibition assays are performed as described above using 50-500 µM inhibitor cephalosporin, 0.5-5 volume percent DMSO cosolvent, and the same amount of enzyme as used in the control assay in buffer (either 50 mM, pH 7.0 sodium phosphate or 100 mM, pH 7.0 Trisma buffer supplemented with 100 µM ZnCl2) at 30° C. The reaction is initiated by after 10 minutes points by the addition and mixing of an appropriate amount of Chromacef to give a 300 µM concentration and the formation of product is followed as a function of time by monitoring the increase in absorbance at 442 nm as a function of time. The reaction is followed through <10% completeness and the initial rate determined via linear least squares analysis where the slope is the initial rate.

The concentration of cephalosporin inhibitor is varied until 50% inhibition is achieved. Where cephalosporin inhibitor concentrations resulted in slightly greater and slightly less than 50% inhibition, the $IC_{50}$ value was determined by interpolation. Representative $IC_{50}$ values thus determined are shown in the Table 1 for 3-(4-(chloromethyl) styryl)-7-(2-phenylacetamido)-ceph-3-em-4-carboxylic acid inhibition (compound of Formula II-Cl/benzyl and the 3-(2-nitro-4-(chloromethyl)styryl)-7-(2-phenylacetamido)-ceph-3-em-4-carboxylic acid (compound of Formula III-Cl/benzyl) inhibition of the metallo-β-lactamases NDM-1, IMP-1, and VIM-2 and of the serine-β-lactamases TEM-26 and KPC-3.

TABLE 1

10 Minute $IC_{50}$ Values mg/L

| | Compound II-Cl/benzyl | Compound III-Cl/benzyl |
|---|---|---|
| NDM-1 | 3 | 0.3 |
| IMP-1 | 29 | 0.3 |
| VIM-2 | 5 | ND |
| TEM-26 | ND | 25 |
| KPC-3 | ND | 0.5 |

Assay for Determining Irreversible β-Lactamase Inhibition

The 100% activity control is performed as described above using 300 µM Chromacef, 3 volume percent DMSO cosolvent in buffer (either 50 mM, pH 7.0 sodium phosphate or 100 mM, pH 7.0 Trisma buffer supplemented with 100 µM $ZnCl_2$) at 30° C. The reaction is initiated by addition and mixing of an appropriate amount of β-lactamase and the formation of product is followed as a function of time by monitoring the increase in absorbance at 442 nm as a function of time. The reaction is followed through <10% completeness and the initial rate determined via linear least squares analysis where the slope is the initial rate.

Figure 2:
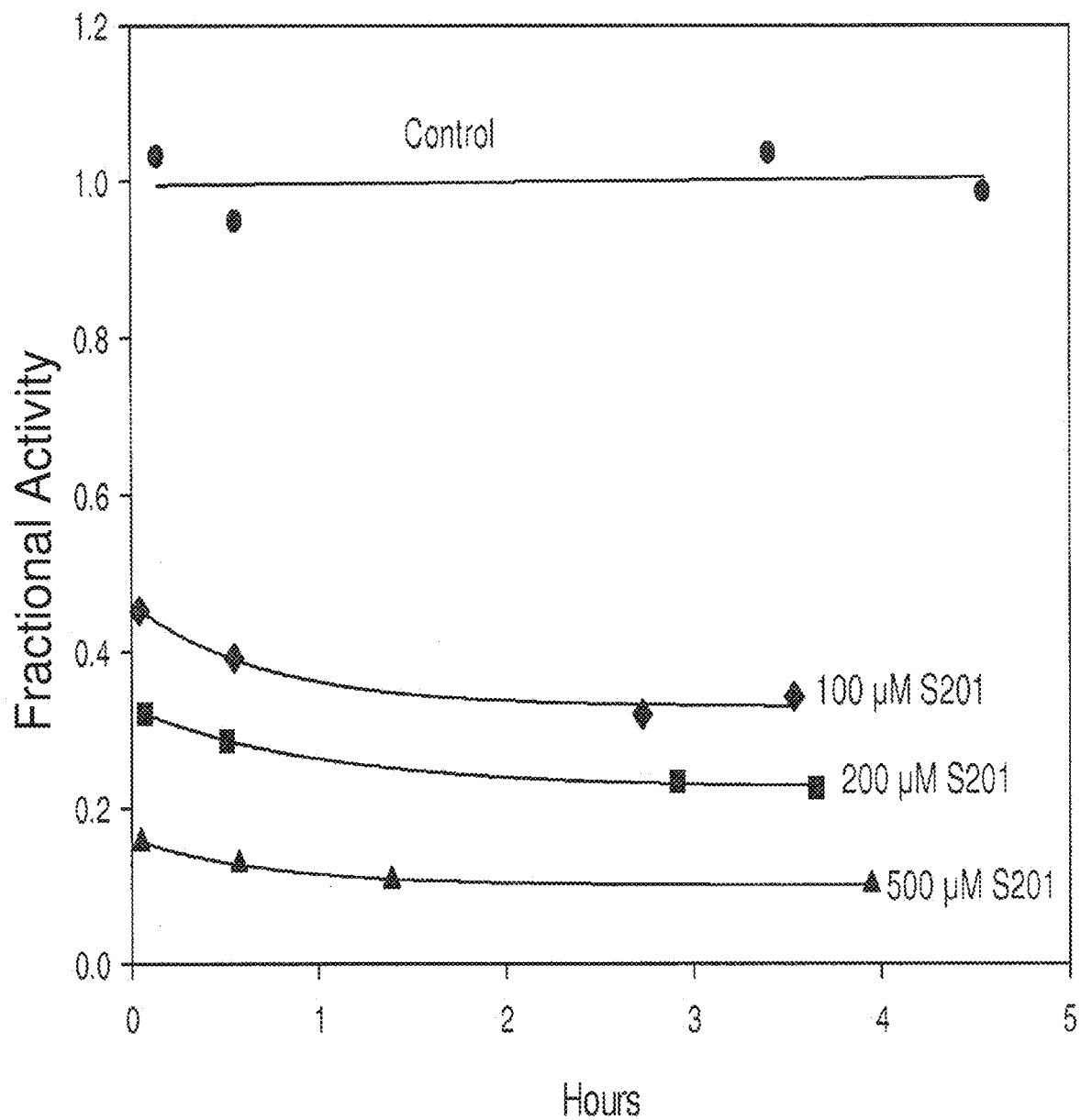
FIG. 2 is a graphic illustration of the concentration and time-dependent inhibition or inactivation of NDM-1 group 3a metallo-P-lactamases by compound III Cl/benzyl. It further demonstrates irreversibility of the inactivation.

Inhibition of β-lactamase was performed at a concentration of β-lactamase 500 times greater than used in the control assay, and 50-500 µM cephalosporin inhibitor, buffer (either 50 mM, pH 7.0 sodium phosphate or 100 mM, pH 7.0 Trisma buffer supplemented with 100 µM $ZnCl_2$), 0.5-5 volume percent DMSO cosolvent for various times. Activity assays were performed the same as the control reaction except 2.00 µL of this inhibition solution were substituted for the uninhibited enzyme solution resulting in a 500-fold dilution of inhibitor to eliminate any competitive binding of inhibitor to enzyme. Representative results for this type of inhibition for the 3-(2-nitro-4-(chloromethyl)styryl)-7-(2-phenylacetamido)-ceph-3-em-4-carboxylic acid (compound of Formula III-Cl/benzyl) inhibition of the metallo-β-lactamase in presented FIG. 2. FIG. 2 demonstrates both the irreversibility of the inhibition and time-dependency of the inhibition.

Assay for Determining Mechanism-Based Inhibition Partition Ratio

The 100% activity control is performed as described above using 300 µM Chromacef, 3 volume percent DMSO cosolvent in buffer (either 50 mM, pH 7.0 sodium phosphate or 100 mM, pH 7.0 Trisma buffer supplemented with 100 µM $ZnCl_2$) at 30° C. The reaction is initiated by addition and mixing of an appropriate amount of β-lactamase and the formation of product is followed as a function of time by monitoring the increase in absorbance at 442 nm as a function of time. The reaction is followed through <10% completeness and the initial rate determined via linear least squares analysis where the slope is the initial rate.

Inhibition of β-lactamase was performed in a concentration of β-lactamase 500 times greater than used in the control assay, and 50-500 µM cephalosporin inhibitor, buffer (either 50 mM, pH 7.0 sodium phosphate or 100 mM, pH 7.0 Trisma buffer supplemented with 100 µM $ZnCl_2$), 0.5-5 volume percent DMSO cosolvent for various times. Activity assays were performed the same as the control reaction except 2.00 µL of this inhibition solution were substituted for the uninhibited enzyme solution resulting in a 500-fold dilution of inhibitor to eliminate any competitive binding of inhibitor to enzyme.

Figure 3:
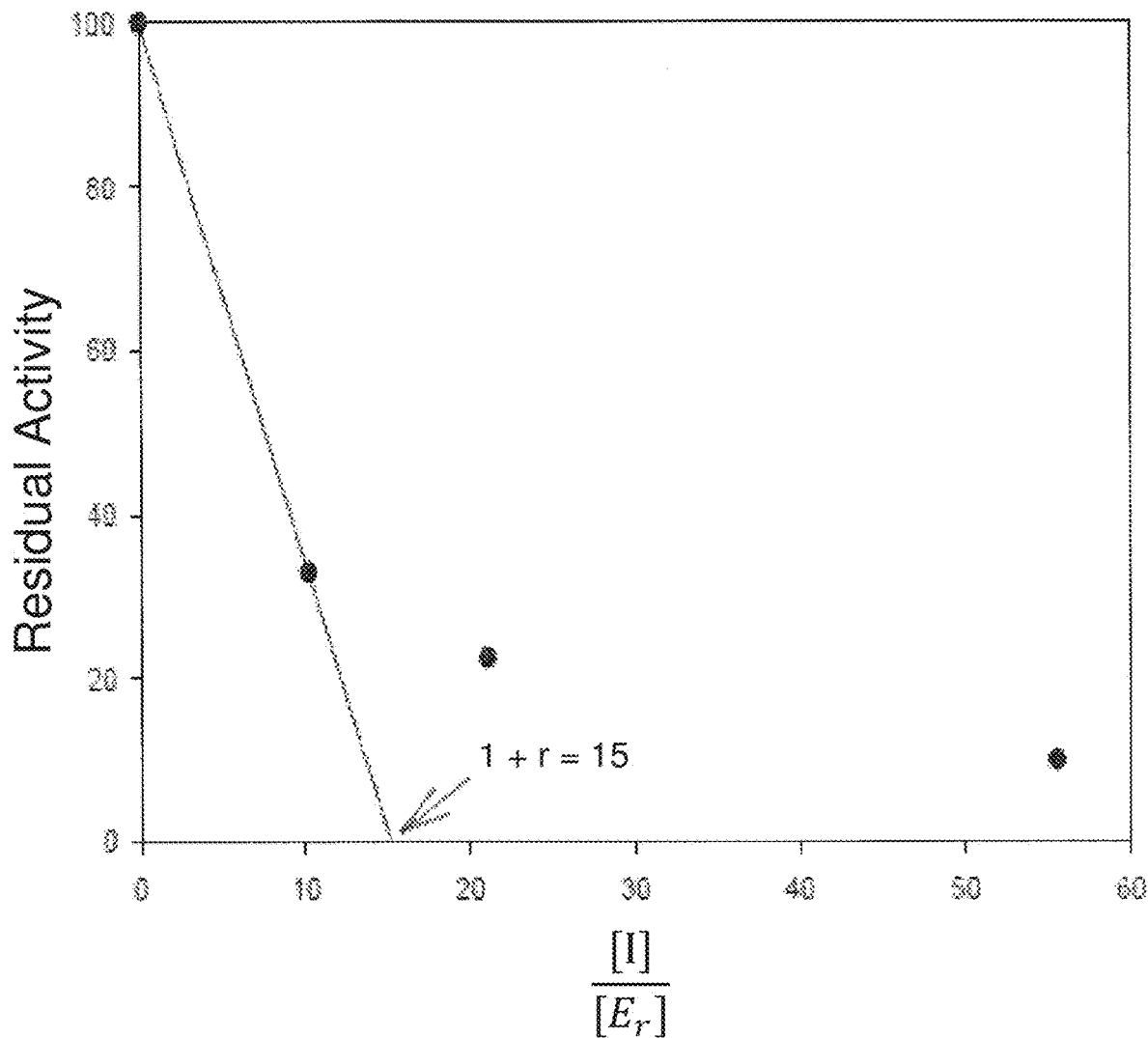
FIG. 3 shows a graph demonstrating the estimation of the partition ratio for the NDM-1 inhibition by compound III of 14.

The partition ratio for mechanism-based inhibition was determined according to a method well known to those skilled in the art (see McDonald, A G; Tipton, K F. (June 2012) Enzymes: Irreversible Inhibition. In: eLS. John Wiley & Sons Ltd, Chichester. http://www.els.net [doi: 10.1002/9780470015902.a0000601.pub2]). The replot of the data in FIG. 2 is shown in FIG. 3, where the x-intercept determined by fitting a line through the linear portion of the plot represents r-1. The partition ration for the 3-(2-nitro-4-(chloromethyl)styryl)-7-(2-phenylacetamido)-ceph-3-em-4-carboxylic acid (compound of Formula III-Cl-benzyl) inhibition of NDM-1 thus determined is 15.

Representative Synthetic Example: Synthesis of 2-nitro-4-(chloromethyl)benzaldehyde (compound f) Scheme 1.

SCHEME 1 Reaction Scheme

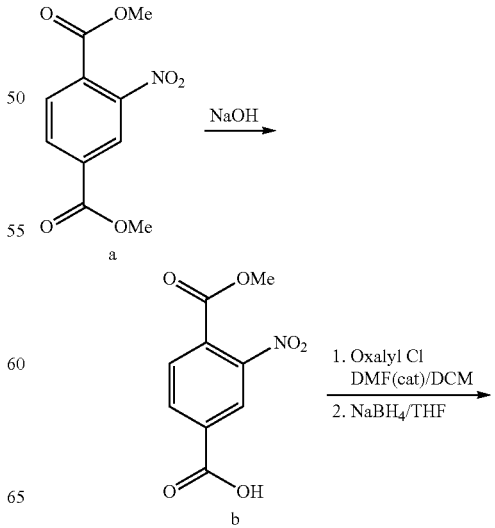

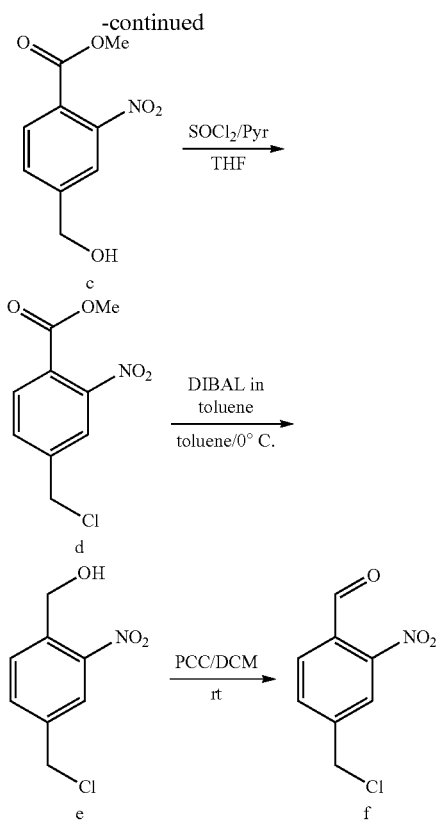

Synthesis of Compound b: 4-(methoxycarbonyl)-3-nitrobenzoic acid

Compound b (4-(methoxycarbonyl)-3-nitrobenzoic acid) was synthesized according to the method of CW Wagner et al. (*J Med Chem* (2009) 52(19) 5950-5966). To a 500 mL round bottom flask charged with dimethylnitroterephthalate (25 g, 104.5 mmol) and dioxane (232 mL) was added 1M NaOH solution dropwise over 30 min over ice bath. Water (100 mL) was added to dilute and the aqueous solution was washed with EtOAc (50 mL×2). The aqueous layer was acidified with 1M HCl (104 mL) to pH 3-4, extracted with EtOAc (150 mL×3). The combined organic layers were dried with $Na_2SO_4$ and then filtered. The filtrate was concentrated and the residue was recrystallized in water to give pure compound b as white crystalline solid (10 g, 42% yield). The $^1H$ NMR is consistent to the literature report. $^1H$ NMR (400 MHz, $CDCl_3$) δ 8.66 (s, 1H), 8.39 (d, J=8.0 Hz, 1H), 7.85 (d, J=8.0 Hz, 1H), 3.98 (s, 3H); MS 226 (M+1).

Synthesis of Compound c: Methyl4-(hydroxymethyl)-2-nitrobenzoate

To a solution of compound b (4-(methoxycarbonyl)-3-nitrobenzoic acid, 9.17 g, 40.7 mmol) in DCM (81 mL), 0.32 mL anhydrous DMF was added at rt under nitrogen atmosphere followed by carefully addition of oxalyl chloride (4.13 mL, 48.8 mmol) over 15 min at room temperature. The reaction mixture was stirred at rt for 2 h and then concentrated over vacuum. The residue was dissolved in 50 mL of anhydrous DCM and the resulting solution was added into a cold suspension of NaBH4 (6.16 g, 126.8 mmol) in 37 mL of anhydrous THF over ice bath. The reaction mixture was stirred over ice bath for 1 h and then quenched with a saturated solution of $NaHCO_3$ (100 mL). The mixture was extracted with EtOAc (200 mL×3). The combined organic layers were washed with a saturated solution of $NH_4Cl$ (100 mL) followed by brine (100 mL) and then dried over $Na_2SO_4$. The suspension was filtered and the filtrate was concentrated to dryness. The residue was purified by flash column with the mobile phase of EtOAc/Hexanes (10% to 30%) to give 7.8 g of a white crystalline solid (compound c) as product. (89% yield, MS: 212=M+1).

Synthesis of Compound d: Methyl 4-(chloromethyl)-2-nitrobenzoate

To a solution of compound c (methyl 4-(hydroxymethyl)-2-nitrobenzoate, 5.0 g, 23.68 mmol) in a mixture of THF (47 mL) and diethyl ether (24 mL), pyridine (0.33 mL, 4.03 Imnol) was added at rt under nitrogen atmosphere followed by a carefully addition of thionyl chloride (3.1 mL, 42.62 mmol) over 10 min at rt. The reaction mixture was stirred at rt for 2 h and then cooled over ice bath. A saturated solution of $NaHCO_3$ (100 mL) was added and extracted by use of EtOAc (100 mL). Two layers were separated and the aqueous phase was extracted with EtOAc (100 mL×2). The combined organic layers were washed with a saturated solution of $NH_4Cl$ (100 mL) followed by brine (100 mL) and then dried over $Na_2SO_4$. The suspension was filtered and the filtrate was concentrated to dryness. The residue was purified by flash column with the mobile phase of EtOAC/Hexanes (5% to 25%) to give 4.8 g of a pale yellow solid (compound d) as the product (88% yield, MS: 230=M+1).

Synthesis of Compound e: 4-(chloromethyl)-2-nitrophenyl methanol

Compound d (methyl-4-(chloromethyl)-2-nitrobenzoate (5.0 g, 21.8 mmol) was dissolved in toluene (109 mL) at rt under $N_2$ atmosphere. The solution was cooled over ice bath and a solution of DIBAL (43.6 mL, 43.6 mmol, 1.0 M in toluene) was added dropwise through a dropping funnel over 60 min by controlling internal temperature below 5° C. The reaction mixture was stirred over an ice bath for 3 h after addition and then quenched with a solution of 20% potassium sodium tartrate (100 mL). EtOAc (100 mL) was added and the reaction mixture was then warmed up to 1i for 3 h. Two layers were separated and the aqueous layer was extracted with EtOAc (100 mL×2). The combined organic layers were washed with a saturated solution of NH4Cl (100 mL) followed by brine (100 mL) and then dried over $Na_2SO_4$. The suspension was filtered and the filtrate was concentrated to dryness. The residue was purified by flash column with the mobile phase of EtOAC/Hexanes (20% to 50%) to give 4.0 g of a white crystalline solid (compound e) as product (91% yield, MS: 202=M+1).

Synthesis of Compound f: 4-(chloromethyl)-2-nitrobenzaldehyde

Commercially available PCC (Pyridinium chlorochromate, 4.81 g, 22.3 mmol) was suspended over DCM (99 mL) at rt under nitrogen atmosphere and stirred for 10 min. Compound 5 (4-(chloromethyl)-2-nitrophenyl methanol, 3.0 g. 14.9 mmol) was then added at once into the reaction mixture. The reaction mixture was stirred for overnight at rt. The reaction mixture was then filtered through a pad of celite. The filter cake was washed with DCM (10 mL×2). The filtrate was washed with a saturated solution of $NaHCO_3$, followed by a solution of brine and dried over $Na_2SO_4$. The suspension was filtered and the filtrate was concentrated to dryness. The residue was purified by CombiFlash with the mobile phase of EtOAc./Hexanes (5% to 30%) to give 1.9 g of a white solid (compound f) as product (64% yield, MS: 200=M+1). $^1H$ NMR ($CDCl_3$, 400 MHz) δ ppm): 10.43 (s, 1H), 8.17 (d, J=1.96 Hz, 1H), 7.98 (d, J=8.2 Hz, 1H), 7.82 (m, 1H), 4.70 (s, 2H), MS: 200=M+1).

Representative Synthetic Example: Synthesis of E,Z p-methoxybenzyl-3-(2-nitro-4-(chloromethyl)styryl)-7-(2-phenylacetamido)-ceph-3-em-4-carboxylate (compound j) Scheme 2.

SCHEME 2

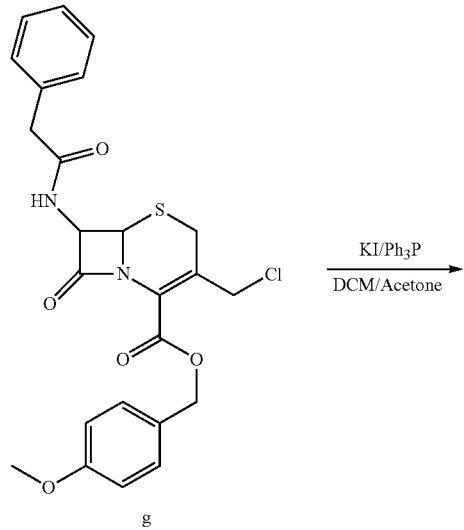

g

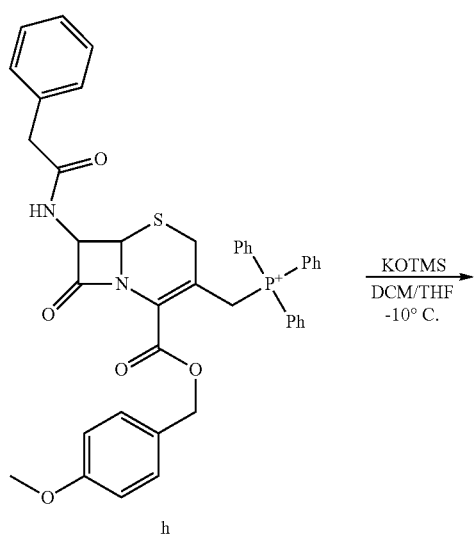

h

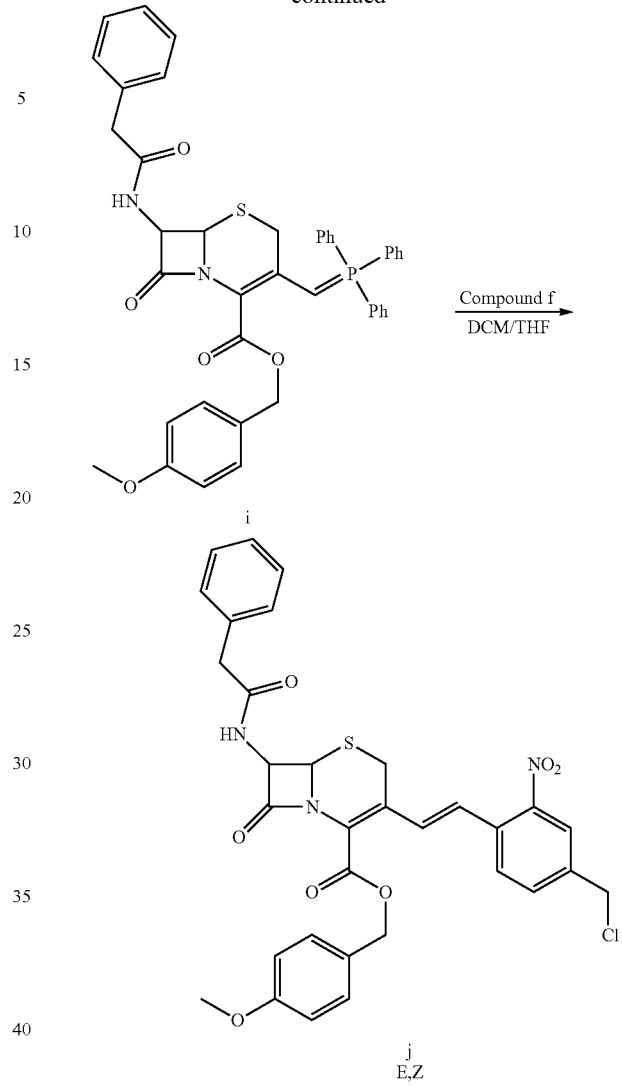

Synthesis of compound j was accomplished by variation of the method reported by Yu and coworkers (Yu S; Vosbeek, A; Corbella, K; Severson, J; Schesser, J; and Sutton, L D. *A chromogenic cephalosporin for β-lactamase inhihitor screening assays* (2012) Analytical Biochemistry, 438, 96-98).

Commercially available compound g (a.k.a. GCLE) is dissolved in a solvent mixture of dichloromethane and acetone along with 5 equivalents of KI and 1 equivalent of triphenylphosphine in an appropriately sized round bottom flask equipped with a magnetic stirring bar. The solution is stirred for 18 hours in the dark. The solution is then gravity filtered to remove any KI and KCl crystals and the solvent evaporated en vacuo. The phosphonium salt (compound h) is used without further work up.

Compound h is then dissolved in a solvent mixture of tetrahydrofuran and dichloromethane and the solution cooled to −10° C. in an ice-brine bath. To the cold solution is added one equivalent of commercially available potassium trimethylsilanoate with stirring and stirred for 1 hour (formation of compound i) at which time 1 equivalent of compound f is added. The reaction mixture is then refluxed with stirring for 5 hours. The reaction mixture is cooled to room temperature and compound j is isolated by flash chromatography using a chloroform-ethylacetate gradient. The solvent is then evaporated en vacuo.

Representative Synthetic Example: Synthesis of E-3-(2-nitro-4-(chloromethyl)styryl)-7-amino-ceph-3-em-4-carboxylic acid Compound j is deprotected by the removal of the p-methyxybenzyl group from the carboxylate by dissolving compound j in 1 mL TFA and 0.5 mL anisole per mmol starting GCLE and stirred for 30 minutes. The solvents are then removed en vacuo and 3-(4-(chloromethyl)styryl)-7-amino-ceph-3-em-4-carboxylic acid is isolated by flash chromatography using acetonitrile as the solvent.

Representative Synthetic Example: Synthesis of 3-(2-nitro-4-(chloromethyl)styyl)-7-((22)-(5-amino-1,2,4-thiadiazol-3-yl)(methoxyimino)ethanamide)-ceph-3-em-4-carboxylic acid (compound n) Scheme 3.

SCHEME 3

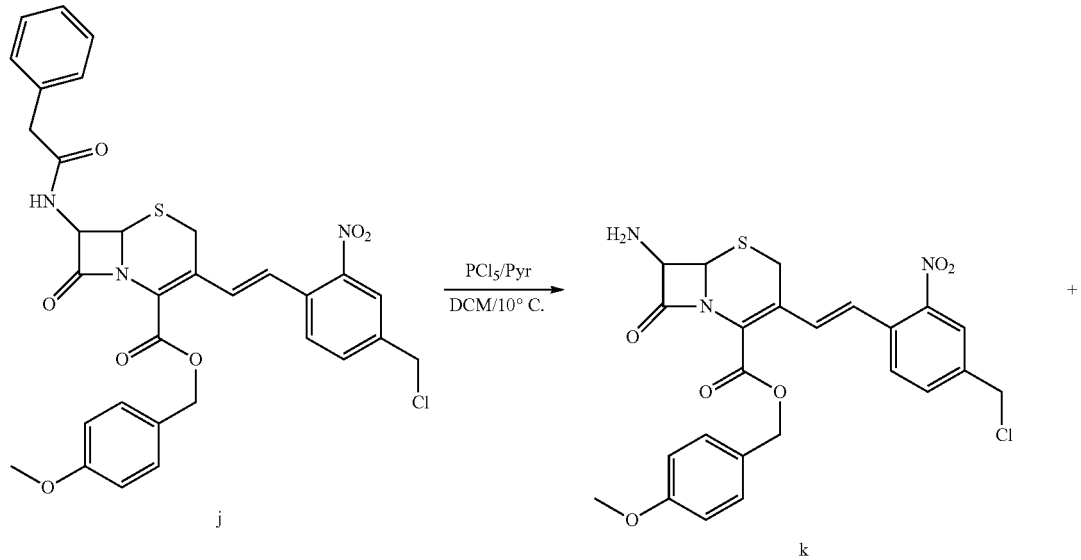

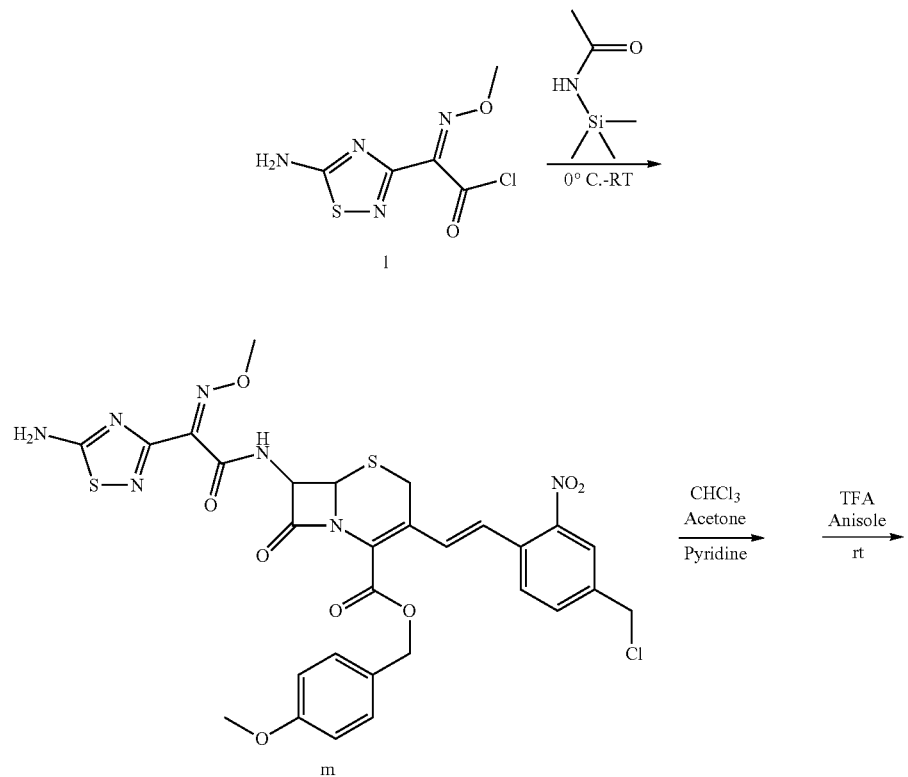

-continued

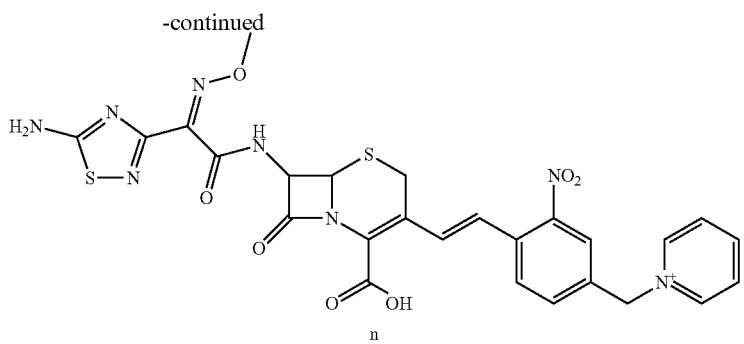

Compound j is dissolved in dichloromethane and cooled to 10° C. when phosphorus pentachloride and pyridine is added to remove the phenylacetate group. The product, compound k, is isolated by flash chromatography and recrystallization. Compound k is then reacted with compound 1 in the presence of trimethylsilylacetamide in THF to afford the product, compound m. The title compound n is then deprotected and purified as in TFA/anisole.

Representative Synthetic Example: Synthesis of (2Z)-(5-amino-1,2,4-thiadiazol-3-yl)(methoxyimino)ethanoyl chloride (compound 1)

The commercially available (2Z)-(5-amino-1,2,4-thiadiazol-3-yl)(methoxyimino)ethanoic acid is transformed into the acid chloride by reacting it with trichlorophosphonate in DMF. The product, compound 1, is then reacted immediately with compound k without isolation.

Representative Synthetic Example: Synthesis of 3-(2-nitro-4-(pyridinium methyl)styryl)-7-((2Z)-(5-amino-1,2,4-thiadiazol-3-yl)(methoxyimino)ethanamide)-ceph-3-em-4-carboxylic acid Compound m is dissolved in a solvent mixture of acetone and chloroform to which is added 5 equivalents of KI and 1 equivalent of pyridine. The mixture is allowed to react with stirring in the dark for 18 hours. The mixture is filtered to remove any excess KI and solvents removed en vacuo. The residue is then dissolved in TFA/anisole as described above to remove the p-methoxybenzyl protective group. The title compound (compound n) is isolate by flash chromatography.

We claim:

1. A compound of formula:

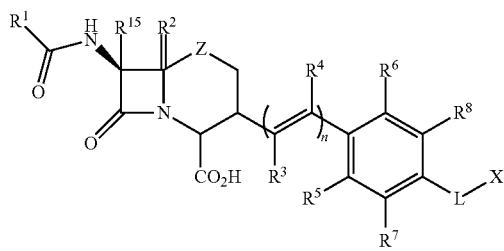

or pharmacologically acceptable salts thereof wherein:
$R^2$, $R^3$, $R^4$, $R^5$, $R^7$, $R^8$ and $R^{16}$ are hydrogen;
$R^6$ is hydrogen or $NO_2$;
L is —$CH_2$;
n is 0 or an integer number ranging from 1 to 5;
Z is —S—;

X is

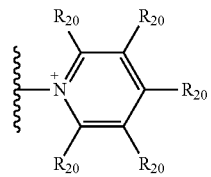

wherein,
each $R_{20}$ independently is selected from hydrogen or two adjacent $R_{20}$ together with the atoms to which they are attached form a 5-6 member carbocyclic or heterocyclic ring which may contain one or more double bonds or be aromatic; and $R^1$ is a pharmacologically acceptable functional group which is a functionalized imine selected from the group consisting of

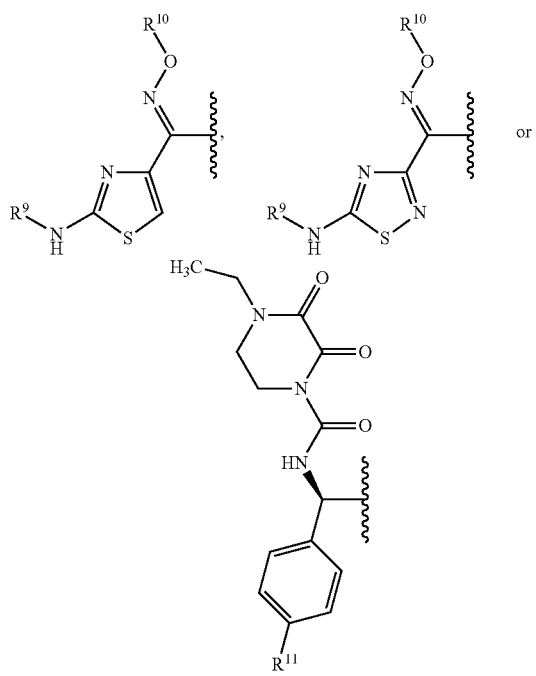

wherein $R^9$ is hydrogen and $R^{10}$ is C1-C6 alkyl or C1-C6 carboxylic acid.

2. A pharmaceutical composition comprising a therapeutically effective amount of one or more compounds of claim 1.

3. A method of treatment of infections, which comprises the step of administering a therapeutically effective amount of one or more compounds of claim 1 to an individual in need of treatment.

4. A method of inhibiting the growth of a microorganism which comprises the step of contacting the microorganism with an effective amount of one or more compounds of claim 1.

5. A method for inhibiting a beta-lactamase which comprises the step of contacting the beta-lactamase with an effective amount of a compound of claim 1.

6. The compound of claim 1, wherein $R^6$ is hydrogen.

7. The compound of claim 1, wherein $R^6$ is $NO_2$.

8. The compound of claim 1, wherein n is 1.

9. The compound of claim 1, wherein n is 0.

10. The compound of claim 1, wherein $R^{10}$ is C1-C6 alkyl.

11. The compound of claim 1, wherein $R^{10}$ is C1-C6 carboxylic acid.

* * * * *